United States Patent
Chen et al.

(10) Patent No.: US 7,482,345 B2
(45) Date of Patent: Jan. 27, 2009

(54) P38 KINASE INHIBITING AGENTS

(76) Inventors: Meng-Hsin Chen, Merck & Co., Inc., P.O. Box 2000, Rahway, NJ (US) 07065-0907; James B. Doherty, Merck & Co., Inc., P.O. Box 2000, Rahway, NJ (US) 07065-0907; Robert Tynebor, Merck Research Laboratories, Sumneytown Pike, P.O. Box 4, West Point, PA (US) 19486

(*) Notice: Subject to any disclaimer, the term of this patent is extended or adjusted under 35 U.S.C. 154(b) by 0 days.

(21) Appl. No.: 11/602,782

(22) Filed: Nov. 21, 2006

(65) Prior Publication Data

US 2007/0129372 A1 Jun. 7, 2007

Related U.S. Application Data

(60) Provisional application No. 60/742,225, filed on Dec. 5, 2005.

(51) Int. Cl.
*A61K 31/53* (2006.01)
*A61K 31/5025* (2006.01)
*A61K 31/4985* (2006.01)
*A61K 31/4375* (2006.01)
*C07D 401/06* (2006.01)
*C07D 401/12* (2006.01)
*C07D 401/10* (2006.01)
*C07D 401/14* (2006.01)
*C07D 421/06* (2006.01)
*C07D 421/10* (2006.01)
*C07D 421/12* (2006.01)
*C07D 421/14* (2006.01)
*C07D 487/04* (2006.01)
*C07D 471/04* (2006.01)

(52) U.S. Cl. .................. 514/248; 544/349; 544/235; 544/183; 544/224; 546/138; 546/345; 546/14

(58) Field of Classification Search .................. 544/235; 514/252.04, 248
See application file for complete search history.

(56) References Cited

U.S. PATENT DOCUMENTS

2007/0117839 A1* 5/2007 Kimura et al. .............. 514/306

FOREIGN PATENT DOCUMENTS

EP 0 294 599 A2 5/1988
WO WO 00/17204 A1 3/2000
WO WO 2005/007632 A1 1/2005
WO WO 2005/034869 A2 4/2005
WO WO 2007/021710 A1 2/2007

OTHER PUBLICATIONS

Columbia University College of P & S Complete Home Medical Guide entry for Arthritis, Prevention, http://cpmcnet.columbia.edu/texts/guide/hmg25_0006.html downloaded Mar. 5, 2003.*
Medline Medical Encyclopedia entry for Ankylosing spondylitis (an alternative name for rheumatoid spondylitis), http://www.nlm.nih.gov/medlineplus/ency/article/000420.htm.*
Osteoarthritis Treatment, http://www.podiatrychannel.com/osteoarthritis/treatment.shtml#prevention, downloaded Mar. 5, 2003.*
Medline Medical Encyclopedia entry for Acute gouty arthritis http://www.nlm.nih.gov/medlineplus/ency/article/000422.htm.*
Johnson, et al., Science, vol. 298, Dec. 6, 2002, 1911-1912.*
Seto, et al., J Clin Invest. 2004, 113(5): 718-726.*
Liu-Bryan, et al., Joint Bone Spine, vol. 72, #4, Jul. 2005, 295-302.*
Westra, et al., Ann. Rheum. Dis. 2004;63:1453-1459.*
Natarajan, et al., "Synthesis of the 2H-quinolizin-2-one scaffold via a stepwise acylation—intramolecular annulation strategy", Elsevier, Tetrahedron Letters 47 (2006) 5063-5067, May 2006.

* cited by examiner

*Primary Examiner*—Mark L Berch
*Assistant Examiner*—Cecilia M Jaisle
(74) *Attorney, Agent, or Firm*—Curtis C. Panzer; Valerie J. Camara

(57) ABSTRACT

Compounds described by the chemical formula (I) or pharmaceutically acceptable salts thereof:

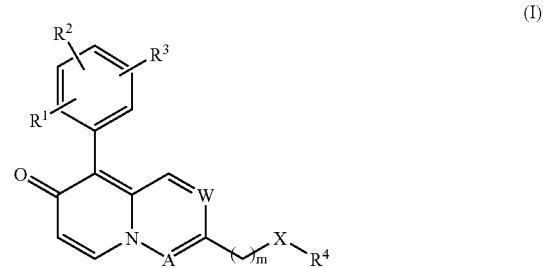

are inhibitors of p38 and are useful in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

11 Claims, No Drawings

P38 KINASE INHIBITING AGENTS

This application claims the benefit of U.S. provisional application Ser. No. 60/742,225, filed Dec. 5, 2005.

BACKGROUND OF THE INVENTION

The present invention relates to heterobicyclic compounds that inhibit the action of the p38 mitogen-activated protein kinase, a mammalian protein kinase that is involved in cell proliferation, cell response to stimuli, and cell death. In particular, this invention relates to heterobicyclic compounds that are selective and potent inhibitors of the p38 mitogen-activated protein kinase. This invention also relates to pharmaceutical compositions containing such heterobicyclic compounds that inhibit the p38 mitogen-activated protein kinase.

RELATED BACKGROUND

Mitogen-activated protein ("MAP") kinases mediate the surface-to-nucleus signal transduction in a cell. Protein kinases that activate and phosphorylate MAP are known as mitogen-activated protein kinase kinases ("MKK"). One such MKK specifically phosphorylates and activates the p38 MAP kinase ("p38") and is called MKK3. U.S. Pat. Nos. 5,736,381 and 5,804,427 describe human mitogen-activated kinase kinase isoforms. International Publication No. 98/00539 describes a human gene encoding an MKK3-Interacting Protein.

Xia et al., Science, 270, 1326-1331 (1995) describes the p38 signal transduction pathway as being activated by proinflammatory cytokines and environmental stress. MKK3 is described as being involved in transducing stress signals such as nerve growth factor mediated apaptosis in PC12 cells. It is believed that inhibition of p38 activity can provide relief from acute and chronic inflammation by blocking production of cytokines such as IL-1 and TNF, thereby inhibiting the production of proinflammatory cytokines such as IL-6 and IL-8. In particular, it is believed that p38 inhibitors block the synthesis of TNFα and IL-1β cytokines, thereby providing relief from inflammatory diseases such as arthritis. Accordingly, it would be desirable to provide novel compounds that are selective and potent inhibitors of the action of p38.

International Publication No. 97/22704 describes the mitogen-activated protein kinase kinase MEK6, which can stimulate phosphorylation and activation of p38 substrates. International Publication Nos. 95/31451, 99/00357 and 98/27098 describe various inhibitors of p38. Nonetheless, there remains a great need to develop inhibitors of the action of p38 for various pharmaceutical and therapeutic applications.

SUMMARY OF THE INVENTION

Compounds described by the chemical formula (I) or pharmaceutically acceptable salts thereof:

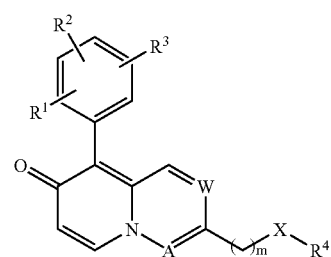

are inhibitors of p38.

DETAILED DESCRIPTION OF THE INVENTION

The present invention provides P38 inhibitor compounds of the chemical formula (I):

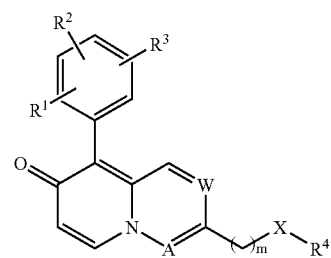

or a pharmaceutically acceptable salt thereof, wherein:
A is selected from the group consisting of —CH— and —N—;
W is selected from the group consisting of —$CR^a$— and —N—;
X is absent or is selected from the group consisting of:
(1) O,
(2) $C_1$-$C_4$ alkyl,
(3) $S(O)_n$,
(4) $C_2$-$C_6$ alkene,
(5) C(O),
(6) $CHR^a$,
(7)

(8) $N(R^a)_{0-2}$,
(9) aryl, and
(10) heteroaryl, said aryl and heteroaryl are each optionally substituted with one or more substituents selected from $R^5$ and $R^6$;
$R^a$ is selected from the group consisting of:
(1) hydrogen,
(2) $C_1$-$C_6$ alkyl,
(3) $C_1$-$C_6$ alkoxy,
(4) $CONH_2$,
(5) $C(O)_2R^4$,
(6) $C_0$-$C_4$alkyl-OH, (7) O—$C_1$-$C_4$ alkyl,
(8) halogen,
(9) aryl,
(10) heteroaryl,
(11) heterocycloalkyl,
(12) $COR^4$,
(13) O—$C_1$-$C_4$alkyl-N—C(O)—$C_0$-$C_2$alkyl($R^cR^d$)—$NH_2$,
(14) heterocycloalkyl-C(O)—$C_0$-$C_2$alkyl($R^cR^d$)—$NH_2$,
(15) $N(R^4)(R^4)$,
(16) O—$R^4$,
(17) N—C(O)—N-heterocycloalkyl,
(18) O—C(O)—N-heterocycloalkyl,
(19) N—$C_1$-$C_4$alkyl-N—$R^4$, and
(20) N—$C_1$-$C_4$alkyl-O—$R^4$;

said heteroaryl and aryl are each optionally substituted with one or more substituents selected from $R^5$ and $R^6$;

$R^c$ and $R^d$ are each independently selected from hydrogen, $C_1$-$C_6$ alkyl, $C_1$-$C_6$ alkoxy, and O—$C_1$-$C_6$ alkyl, or $R^c$ and $R^d$ can join together with the carbon atom to which they are attached to form a ring selected from the group consisting of cycloalkyl and heterocycloalkyl;

$R^1$, $R^2$ and $R^3$ are each independently selected from the group consisting of:
(1) hydrogen,
(2) $C_1$-$C_6$ alkoxy,
(3) $C_3$-$C_6$ cycloalkyl,
(4) heteroaryl,
(5) CN,
(6) halogen,
(7) $C_1$-$C_6$ alkyl,
(8) $C_2$-$C_6$ alkene,
(9)

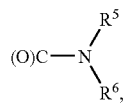

(10) C(O)—$R^4$,
(11) aryl,
(12) $OR^4$,
(13) $CON(R^4)_2$,
(14) $N(R^4)_2$,
(15) $C_1$-$C_4$—OH,
(16) heterocycloalkyl,
(17) CON-alkyl-$CO_2$—$R^4$,
(18) CON-alkyl-$CON(R^4)_2$,
(19) CON-alkyl-$N(R^4)_2$, and
(20) $C(O)_2$—$R^4$ said aryl, heteroaryl, heterocycloalkyl, and cycloalkyl are each optionally substituted with one or more substituents selected from $R^5$ and $R^6$;

$R^4$ is selected from the group consisting of:
(1) aryl,
(2) hydrogen,
(3) halogen,
(4) heteroaryl,
(5) $C_1$-$C_6$ alkyl-aryl,
(6) $C_3$-$C_6$ cycloalkyl,
(7) $C_1$-$C_6$ alkyl,
(8) $C_1$-$C_6$ alkyl-$C_3$-$C_6$ cycloalkyl,
(9) $C_1$-$C_6$ alkyl-heteroaryl, (10)

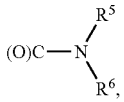

(11) C(O)—$R^5$,
(12) NH—$C_1$-$C_4$ alkyl,
(13) NH-aryl,
(14) $C_1$-$C_4$ alkyl-heterocycloalkyl,
(15) heterocycloalkyl,
(16) $C_0$-$C_4$alkyl-$NH_2$, and
(17) $C_0$-$C_4$alkyl-OH;

said heteroaryl, aryl, heterocycloalkyl and cycloalkyl are each optionally substituted with one or more substituents selected from $R^5$ and $R^6$;

$R^5$ and $R^6$ are each independently selected from:
(1) hydrogen,
(2) halogen,
(3) $C_1$-$C_6$ alkoxy,
(4) aryl,
(5) $C_3$-$C_6$ cycloalkyl,
(6) $C_1$-$C_6$ alkyl, and
(7) heteroaryl, said heteroaryl and aryl are each optionally substituted with one or more substituents selected from $R^7$, or $R^5$ and $R^6$, together with the nitrogen atom to which they are attached, can join to form a 5- to 7-membered heteroaryl or heterocycloalkyl $R^7$ is selected from the group consisting of:
(1) hydrogen,
(2) halogen,
(3) aryl,
(4) $C_3$-$C_6$ cycloalkyl,
(5) NH—$C_1$-$C_4$ alkyl,
(6) $C_1$-$C_6$ alkyl,
(7) heteroaryl,
(8) $C_1$-$C_4$alkyl-heterocycloalkyl,
(9) heterocycloalkyl,
(10) $C_0$-$C_4$alkyl-$NH_2$, and
(11) $C_0$-$C_4$alkyl-OH;

m is 0, 1, 2, or 3; and
n is 0, 1, or 2.

A first embodiment of the present invention includes compounds wherein A is N.

A second embodiment of the present invention includes compounds wherein X is selected from the group consisting of O, NH and $CH_2$.

A third embodiment of the present invention includes compounds wherein X is O.

A fourth embodiment of the present invention includes compounds wherein X is NH.

A fifth embodiment of the present invention includes compounds wherein X is $CH_2$.

A sixth embodiment of the present invention includes compounds wherein $R^1$, $R^2$ and $R^3$ are each independently selected from the group consisting of:
(1) hydrogen,
(2) $C_1$-$C_6$ alkoxy,
(3) heteroaryl,
(4) halogen,
(5) aryl
(6) CN, (7) $C_1$-$C_6$ alkyl,
(8) $C_2$-$C_6$ alkene,
(9)

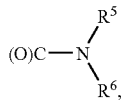

and
(10) $C(O)_2$—$R^4$, said heteroaryl and aryl is optionally substituted with one or more substituents selected from selected from $R^5$ and $R^6$.

A seventh embodiment of the present invention includes compounds wherein $R^1$, $R^2$ and $R^3$ are each independently selected from the group consisting of:
(1) hydrogen,
(2) $C_1$-$C_6$ alkoxy,
(3) heteroaryl,
(4) halogen,
(5)

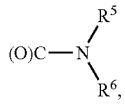

and
(6) $C(O)_2$—$R^4$, said heteroaryl is optionally substituted with one or more substituents selected from selected from $R^5$ and $R^6$.

An eighth embodiment of the present invention includes compounds wherein $R^4$ is selected from the group consisting of:
(1) aryl,
(2) $C_1$-$C_6$ alkyl-aryl,
(3) $C_3$-$C_6$ cycloalkyl,
(4) $C_1$-$C_6$ alkyl,
(5) $C_1$-$C_6$ alkyl-$C_3$-$C_6$ cycloalkyl,
(6)

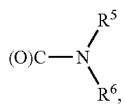

and
(7) $C(O)$—$R^5$, said aryl and cycloalkyl are each optionally substituted with one or more substituents selected from $R^5$ and $R^6$.

A ninth embodiment of the present invention includes compounds wherein $R^5$ and $R^6$ are each independently selected from the group consisting of:
(1) hydrogen,
(2) halogen,
(3) $C_1$-$C_6$ alkoxy,
(4) $C_3$-$C_6$ cycloalkyl, (5)

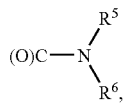

and
(6) $C_1$-$C_6$ alkyl;

said heteroaryl and aryl are each optionally substituted with one or more substituents selected from $R^7$, or $R^5$ and $R^6$, together with the nitrogen atom to which they are attached, can join to form a 5- to 7-membered heteroaryl or heterocycloalkyl.

A tenth embodiment of the present invention includes compounds wherein $R^7$ is selected from the group consisting of:
(1) hydrogen,
(2) halogen,
(3) aryl, and
(4) $C_1$-$C_6$ alkyl.

Additional embodiments of the present invention include compounds of the Formula Ia:

(Ia)

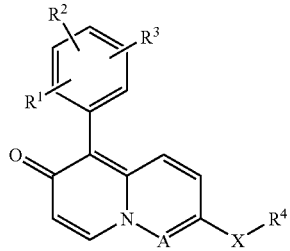

or a pharmaceutically acceptable salt thereof, wherein $R^1$, $R^2$, $R^3$, $R^4$, A and X are as defined in Formula I.

Further embodiments of the present invention include compounds of the Formula Ib:

(Ib)

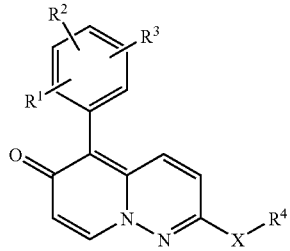

or a pharmaceutically acceptable salt thereof, wherein $R^1$, $R^2$, $R^3$, $R^4$ and X are as defined in Formula I.

Further embodiments of the present invention include compounds of the Formula Ic:

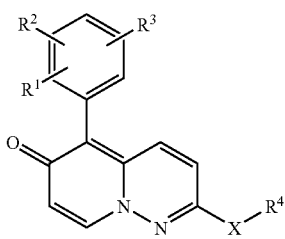

(Ic)

or a pharmaceutically acceptable salt thereof, wherein $R^1$, $R^2$, $R^3$, and $R^4$ are as defined in Formula I, and X is selected from $CH_2$ and O.

Still further embodiments of the present invention include compounds of the Formula Id:

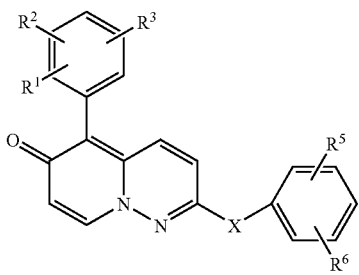

(Id)

or a pharmaceutically acceptable salt thereof, wherein $R^1$, $R^2$, R3, $R^5$ and $R^6$ are as defined in Formula I, and X is selected from $CH_2$ and O.

Additional embodiments of the present invention include compounds of the Formula Ie:

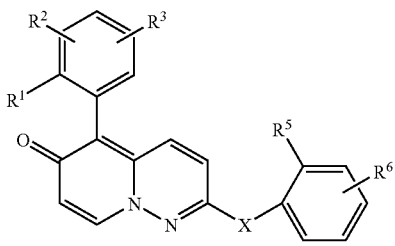

(Ie)

or a pharmaceutically acceptable salt thereof, wherein $R^1$, $R^2$, $R^3$, $R^5$ and $R^6$ are as defined in Formula I, and X is selected from $CH_2$ and O.

Within this embodiment is the genus wherein
$R^1$, $R^2$ and $R^3$ are each independently selected from the group consisting of:
(1) hydrogen,
(2) $C_1$-$C_6$ alkoxy,
(3) heteroaryl,
(4) halogen,
(5) aryl
(6) CN,
(7) $C_1$-$C_6$ alkyl,
(8) $C_2$-$C_6$ alkene, (9)

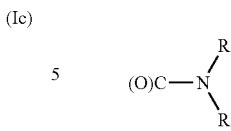

and

(10) $C(O)_2$—$R^4$, said heteroaryl and aryl is optionally substituted with one or more substituents selected from selected from $R^5$ and $R^6$.

Within this genus there is a sub-genus wherein
$R^1$, $R^2$ and $R^3$ are each independently selected from the group consisting of:
(1) hydrogen,
(2) $C_1$-$C_6$ alkoxy,
(3) heteroaryl,
(4) halogen,
(5) $C_2$-$C_6$ alkene,
(6)

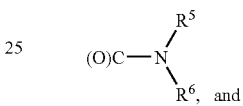

and (7) $C(O)_2$—$R^4$, said heteroaryl is optionally substituted with one or more substituents selected from selected from $R^5$ and $R^6$.

Within this sub-genus there is a class wherein
$R^4$ is selected from the group consisting of:
(1) aryl,
(2) $C_1$-$C_6$ alkyl-aryl,
(3) $C_3$-$C_6$ cycloalkyl,
(4) $C_1$-$C_6$ alkyl,
(5) $C_1$-$C_6$ alkyl-$C_3$-$C_6$ cycloalkyl,
(6)

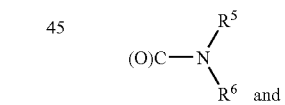

and (7) $C(O)$—$R^5$, said aryl and cycloalkyl are each optionally substituted with one or more substituents selected from $R^5$ and $R^6$.

Within this genus there is another sub-genus wherein
$R^5$ and $R^6$ are each independently selected from the group consisting of:
(1) hydrogen,
(2) halogen,
(3) $C_1$-$C_6$ alkoxy,
(4) $C_3$-$C_6$ cycloalkyl,
(5)

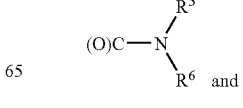

and (6) $C_1$-$C_6$ alkyl;

said heteroaryl and aryl are each optionally substituted with one or more substituents selected from $R^7$, or $R^5$ and $R^6$, together with the nitrogen atom to which they are attached, can join to form a 5- to 7-membered heteroaryl or heterocycloalkyl.

The term "acetal" means a functional group or molecule containing a CH bonded to two —OR groups. A "cyclic acetal" thus means a cyclic or ring structure containing an acetal group.

The term "alkyl" means carbon chains that have no double or triple bonds, and that may be linear or branched or combinations thereof. Thus, $C_1$-$C_6$ alkyl is defined to identify the group as having 1, 2, 3, 4, 5 or 6 carbons in an arrangement that is linear, branched, or a combination thereof. Examples of alkyl groups include methyl, ethyl, propyl, n-propyl, iso-propyl, butyl, sec- and tert-butyl, pentyl, hexyl, heptyl and the like. The term "$C_0$-$C_4$alkyl" includes alkyls containing 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "alkene" means linear or branched structures and combinations thereof, of the indicated number of carbon atoms, having at least one carbon-to-carbon double bond, wherein hydrogen may be replaced by an additional carbon-to-carbon double bond. $C_2$-$C_6$ alkene, for example, includes ethylene, propylene, 1-methylethylene, butylene and the like.

The term "alkynyl" means linear or branched structures and combinations thereof, of the indicated number of carbon atoms, having at least one carbon-to-carbon triple bond. Thus $C_2$-$C_6$ alkynyl is defined to identify the group as having 2, 3, 4, 5 or 6 carbon in a linear or branched arrangement, such that $C_2$-$C_6$ alkynyl specifically includes 2-hexynyl and 2-pentynyl.

The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

The term "amine" unless specifically stated otherwise includes primary, secondary and tertiary amines.

The term "aryl," unless specifically stated otherwise, is intended to mean any stable monocyclic or fused bicyclic carbon ring of up to 7 members in each ring, wherein at least one ring is aromatic. Examples of such aryl elements include phenyl, naphthyl and tolyl.

The term "aryloxy" unless specifically stated otherwise includes multiple ring systems as well as single ring systems such as, for example, phenyl or naphthyl, connected through the oxy connecting atom to the connecting site.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "hetero," unless specifically stated otherwise, includes one or more O, S, or N atoms. For example, heterocycloalkyl and heteroaryl include ring systems that contain one or more O, S, or N atoms in the ring, including mixtures of such atoms. The hetero atoms replace ring carbon atoms.

Examples of heterocycloalkyl include azetidinyl, pyrrolidinyl, piperidinyl, piperazinyl, morpholinyl, tetrahydrofuranyl, imidazolinyl, cyclic acetals, cyclic ketals, pyrolidin-2-one, piperidin-2-one and thiomorpholinyl. As used herein, "heterocycloalkyl" includes bridged heterocycloalkyls having two or more heterocycloalkyl groups joined via adjacent or non-adjacent atoms.

The term "heteroaryl", as used herein except where noted, is intended to mean a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, pyridine, pyrimidine, pyrazine, thiophene, oxazole, thiazole, triazole, thiadiazole, oxadiazole, pyrrole, 1,2,4-oxadiazole, 1,3,4-oxadiazole, 1,2,4-thiadiazole, 1,3,4-thiadiazole, and 1,2,4-triazole.

Additional examples of heteroaryl include quinolinyl, pyrimidinyl, isoquinolinyl, pyridazinyl, quinoxalinyl, furyl, benzofuryl, dibenzofuryl, thienyl, benzothienyl, indolyl, indazolyl, isoxazolyl, isothiazolyl, imidazolyl, benzimidazolyl, thiadiazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Unless otherwise stated, the term "carbamoyl" is used to include —NHC(O)OC1-C4alkyl, and —OC(O)NHC1-C4alkyl.

The term "halogen" includes fluorine, chlorine, bromine and iodine atoms.

The term "ketal" means a functional group or molecule containing a carbon bonded to two —OR groups. A "cyclic ketal" thus means a cyclic or ring structure containing a ketal group.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$)alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Unless specifically stated otherwise or indicated by a bond symbol (dash or double dash), the connecting point to a recited group will be on the right-most stated group. That is, for example, a phenylalkyl group is connected to the main structure through the alkyl and the phenyl is a substituent on the alkyl.

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be mixtures of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomers. All such isomers, including optical isomers, being included in the present invention.

The invention described herein also includes a pharmaceutical composition which is comprised of a compound described by Formula (I), or a pharmaceutically acceptable salt thereof, in combination with a pharmaceutically acceptable carrier.

The invention described herein also includes a pharmaceutical composition which is comprised of a compound described by Formula (I), or a pharmaceutically acceptable salt thereof, in combination with a pharmaceutically acceptable carrier. The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists.

The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention includes methods of treating arthritis by administering to a mammalian patient in need of such treatment a compound described by Formula (I), or a pharmaceutically acceptable salt thereof, in combination or in coadministration with a COX-2 inhibitor.

The invention described herein also includes a method of treating a cytokine mediated disease in a mammal, comprising administering to a mammalian patient in need of such treatment an amount of a compound described by Fonmula (I), or a pharmaceutically acceptable salt thereof, in an amount which is effective to treat said cytokine mediated disease.

Of particular interest is a method of treating inflammation in a mammalian patient in need of such treatment, which is comprised of administering to said patient an anti-inflammatory effective amount of a compound described by Formula (I), or a pharmaceutically acceptable salt thereof.

Another method which is of particular interest is a method of treating a cytokine mediated disease as described herein wherein the disease is osteoporosis.

Another method which is of particular interest is a method of treating a cytokine mediated disease as described herein wherein the disease is non-osteoporotic bone resorption.

Yet another method which is of particular interest is a method of treating a cytokine mediated disease as described herein wherein the disease is Crohn's disease.

This invention also relates to a method of treating arthritis in a mammal in need such treatment, which comprises administering to said mammal an amount of a compound of formula I which is effective for treating arthritis. Such method includes the treatment of rheumatoid and osteoarthritis.

When administered to a patient for the treatment of arthritis, the dosage used can be varied depending upon the type of arthritis, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

This invention also relates to a method of inhibiting the action of p38 in a mammal in need thereof, which comprises administering to said mammal an effective amount of a compound described by Formula (I), or a pharmaceutically acceptable salt thereof, to inhibit said action of p38, down to normal levels, or in some cases to subnormal levels, so as to ameliorate, prevent or treat the disease state.

The compounds of formula 1 can be used in the prophylactic or therapeutic treatment of disease states in mammals which are exacerbated or caused by excessive or unregulated cytokines, more specifically IL-1, IL-6, IL-8 or TNF.

Because the compounds of formula I inhibit cytokines, such as IL-1, IL-6, IL-8 and TNF, by inhibiting the action of p38 the compounds are useful for treating diseases in which cytokine presence or activity is implicated, such as pain, rheumatoid arthritis, rheumatoid spondylitis, osteoarthritis, gouty arthritis and other arthritic conditions.

The compounds described by Formula (I), or a pharmaceutically acceptable salt thereof, are also useful to treat other disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds described by Formula (I), or a pharmaceutically acceptable salt thereof, are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds described by Formula (I), or a pharmaceutically acceptable salt thereof, are also useful in treating diseases such as chronic obstructive pulmonary disease and diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound described by Formula (I), or a pharmaceutically acceptable salt thereof, in an amount which is effective for treating said disease or condition.

The compounds described by Formula (I), or a pharmaceutically acceptable salt thereof, are also useful for treating Alzheimer's disease. The instant invention thus includes a method of treating Alzheimer's disease in a mammal in need of such treatment, which comprises administering to said mammal a compound of Formula (I), or a pharmaceutically acceptable salt thereof, in an amount effective for treating said disease or condition.

When administered to a patient for the treatment of a disease in which a cytokine or cytokines are implicated, the dosage used can be varied depending upon the type of disease, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally advantageous. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, or, advantageously, one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

Assays

Protein Expression and Purification.

Murine p38 containing the FLAG epitope tag was expressed in *Drosophila* S2 cells under transcriptional control of a copper-inducible metallothionein promoter. Expression of recombinant p38 was induced by treating transfected cells with 1 mM $CuSO_4$ for 4 hours. To generate active recombinant murine p38, $CuSO_4$-treated S2 cells were stimulated 10 minutes prior to harvest with 400 mM NaCl, 2 mM $Na_3VO_4$, and 100 µg/L okadaic acid. Cell pellets were washed with phosphate-buffered saline, 2 mM $Na_3VO_4$, and lysed in 20 mM Tris HCl, pH 7.5, 120 mM NaCl, 1% Triton X-100, 2 mM EDTA, 20 mM NaF, 4 mM $Na_3VO_4$, 2 mM Prefabloc SC (Boehringer Mannheim). Cell lysates were centrifuged for 10 min at 13,000×g, and activated, recombinant murine p38 was immunoaffinity purified from the lysate by column chromatography through anti-FLAG M2 resin (Kodak) that had been equilibrated with lysis buffer. After loading the extract the resin was washed with 10 column volumes of lysis buffer, 10 column volumes buffer A (10 mM Tris HCl, pH 7.5, 500 mM NaCl, 20% glycerol) and 10 column volumes of buffer B (10 mM Tris HCl pH 7.5, 150 mM NaCl, 20% glycerol). The fusion protein was eluted in buffer B containing 100 µg/mL FLAG peptide (Kodak).

The N-terminal 115 amino acids of ATF-2 was expressed in *E. coli* as a fusion protein with glutathione-S-transferase. The fusion protein was purified over glutathione agarose according to standard procedures (Pharmacia).

p38 Kinase Assay.

p38 kinase assays were performed in a reaction volume of 100 µL in a 96-well plate, at 30° for 45-1200 min under the following conditions: 25 mM Hepes, pH 7.4, 10 mM $MgCl_2$, 20 mM β-glycerolphosphate, 2 mM DTT, 5 µM ATP, 10 µCi [γ-33P]-ATP and ~2 µM GST-ATF2. Serial dilutions of compounds were added to each reaction in 2 µL DMSO. 2 µL of DMSO was added to the last row of each reaction plate as the no inhibitor control for each inhibitor titration. The reaction was terminated with an equal volume of a stop solution containing 100 mM EDTA and 15 mM sodium pyrophosphate. PVDF filter plates (MAIPNOB50, Millipore) were pre-wet with methanol and washed with the stop solution. 50 µL aliquots from a single reaction were applied to the filter under vacuum, and the filter was washed twice with 75 mM phosphoric acid. The filter plates were counted in a scintillation counter (Top Count, Packard) and the percent inhibition at each compound concentration is determined.

TNF-α Release Assay.

Blood was obtained from healthy volunteers by venipuncture using sodium heparin as an anti-coagulant. Peripheral blood mononuclear cells (PBMCs) were isolated using Lymphocyte Separation Medium (ICN) according to manufacturers specifications. Isolated PBMCs were washed 3 times with HBSS and diluted to a density of $2 \times 10^6$ cells/mL in RPMI+

5% autologous human serum. 50 μL of the serial dilutions of inhibitor were added to wells of a 96-well tissue culture plate followed by addition of 100 μL of PBMCs and then 50 μL of RPMI complete medium containing 400 ng/mL LPS. A control well of cells without compound but with LPS (maximal stimulation control) and one without compound and without LPS (background control) were included in each titration. The cells were incubated for 16 hours in a humidified incubator at 37° C., 5% $CO_2$. Supernatants were then harvested and TNF-α levels were quantified by immunoassay using commercial reagents (R&D, Inc).

The compounds of this invention demonstrated efficacy (IC50) in the above assays by results of less than 10 μM. Advantageous compounds had results less than 1 μM. Even more advantageous compounds had results less than 0.1 μM. Still more advantageous compounds had results in the assays of less than 0.01 μM. The follow are illustrative of the efficacy demonstrated by the specific Examples:

| Example Number | IC50 (nM) |
| --- | --- |
| 4 | 22 |
| 14 | 59 |
| 49 | 710 |
| 52 | 320 |
| 53 | 93 |

The abbreviations used herein are as follows unless specified otherwise:
Bu butyl
Bn benzyl
BOC t-butyloxycarbonyl
BOP benzotriazol-1-yloxy tris/dimethylamino-phosphonium hexafluorophosphate
DCC dicyclohexylcarbodiimide
DME 1,2-dimethoxyethane
DMF N,N-dimethylformamide
DMAP 4-dimethylaminopyridine
EDC 1-(3-dimethylaminopropyl 3-ethylcarbodi-imide hydrochloride
EtOAc ethyl acetate
Eq. equivalent(s)
HOBt, HOBT hydroxybenztriazole
HPLC high pressure liquid chromatography
LAH lithium aluminum hydride
LCMS liquid chromatography-mass spectrophotometer
LHMDS lithium bis(trimethylsilyl)amide
MeOH methanol
MHz megahertz
MS(ES) mass spectrophotometer-electon spray
NMP N-methylpyrrolidinone
Ph phenyl
Pr propyl
TBAF tetrabutylammonium fluoride
TEA triethylamine
THF tetrahydrofuran
TMEDA N,N,N',N'-tetramethylethylenediamine
TLC thin layer chromatography
Tetrakis tetrakis(triphenylphosphine)palladium The present compounds can be prepared according to the general Schemes provided below as well as the procedures provided in the Intermediates and Examples. The following Schemes, Examples and Intermediates further describe, but do not limit, the scope of the invention. The substituents are the same as in the above Formulas except where defined otherwise or otherwise apparent to the ordinary skilled artisan.

The procedures described herein for synthesizing the compounds may include one or more steps of protecting group manipulations and of purification, such as, recrystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1H$ and $^{13}C$ NMR), infrared and ultraviolet spectroscopy (IR and UV), X-ray crystallography, elemental analysis and HPLC and mass spectrometry (LC-MS). Methods of protecting group manipulation, purification, structure identification and quantification are well known to one skilled in the art of chemical synthesis.

It is understood that the functional groups present in compounds described in the Schemes below can be further manipulated, when appropriate, using the standard functional group transformation techniques available to those skilled in the art, to provide desired compounds described in this invention.

Other variations or modifications, which will be obvious to those skilled in the art, are within the scope and teachings of this invention. This invention is not to be limited except as set forth in the following claims.

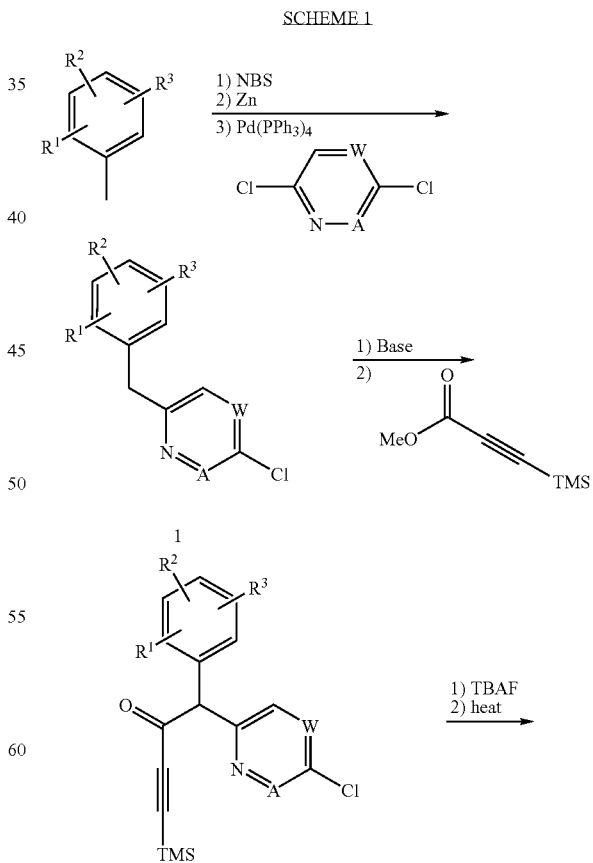

SCHEME 1

-continued

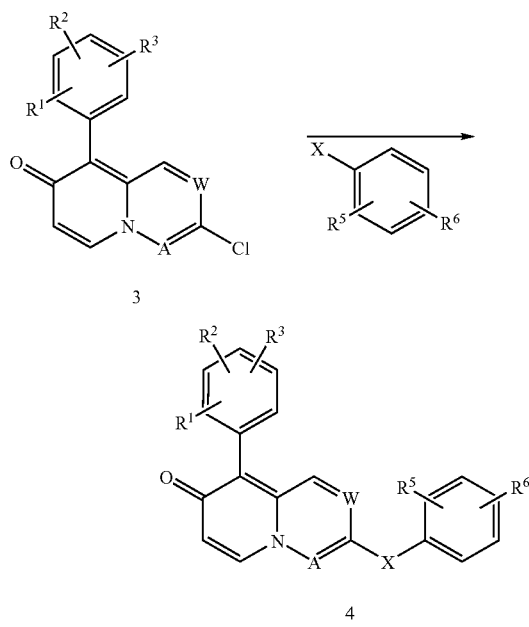

Compound 4 can be synthesized as described in Scheme 1. Compound 1 can be prepared by literature procedures (Minato, A., Tamao, K., Hayashi, T., Suzuki, K., Kumada, M., Tetrahedron Lett., (1980), 21, 845; and Andres, J. I., Alonso, J. M., Fernandez, J., Iturrino, L., Martinez, P., Meert, T. F., Sipido, V. K., Bioorg Med Chem Lett. (2002), 12 (24), 3573-3577). Deprotonation of compound 1, which can be achieved by using a base such as lithium diisopropyl amide and lithium bis(trimethylsilyl)amide, in THF at low temperature and quenching the anion with propynoate to yield compound 2. Removal of the TMS protecting group can be carried out according to known procedures to give the cyclization precursor which can be achieved by heating in an inert solvent such as DMF or NMP, to give compound 3. Compound 4 can be arrived at by using known methods, such as substitution reactions or Pd-mediate coupling reactions.

INTERMEDIATE-1

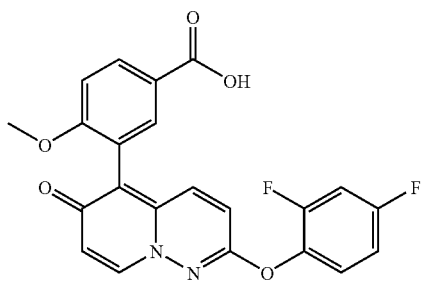

Step-A methyl 3-(bromomethyl)-4-methoxybenzoate

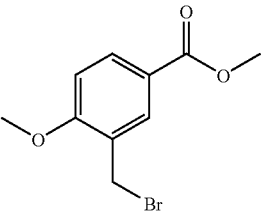

To a solution of methyl 4-methoxy-3-methylbenzoate (10.0 g, 55.6 mmol) dissolved in $CCl_4$ (500 mL) was added N-bromosuccinimide (10.8 g, 61.1 mmol) and benzoyl peroxide (1.30 g, 5.56 mol). The mixture was irradiated with a sunlamp (250 W) to create a gentle reflux. After 2 hours of exposure the reaction was complete by TLC. The reaction mixture was cooled, filtered through celite, and concentrated to yield a white solid.

$^1$H NMR ($CDCl_3$, 500 MHz): 8.05 (m, 2H), 6.94 (d, 1H), 4.58 (s, 2H), 3.98 (s, 3H), 3.90 (s, 3H).

Step-B methyl 3-[(6-chloropyridazin-3-yl)methyl]-4-methoxybenzoate

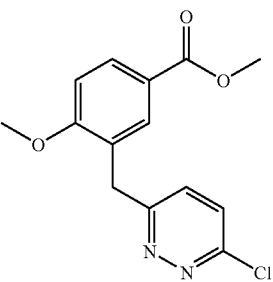

Crude material from Step-A (30.0 g, 116.3 mmol) was dissolved in THF (700 mL) and cooled to 0° C. Activated zinc (Rieke, 5 g zinc/100 mL THF suspension) (11.15 g, 174.4 mmol) was added and the reaction warmed to room temperature over 2 hours. To this mixture was added Tetrakis (5.0 g, 5.8 mmol) and 3,6-dichloro pyridazine (18.0 g, 133.7 mmol), and heated to 75° C. for 0.5 hours until reaction was complete. The reaction was cooled to room temperature, filtered through celite, and concentrated to yield a black oil. The crude residue was purified via silica gel chromatography (hexane/EtOAc).

MS(ES): 293.1 (M+H).

Step-C methyl 3-[1-(6-chloropyridazin-3-yl)-2-oxo-4-(trimethylsilyl)but-3-yn-1-yl]-4-methoxybenzoate

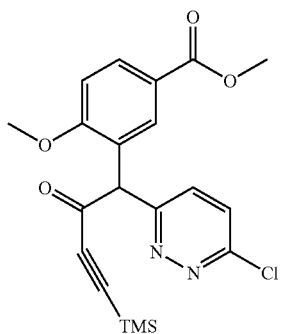

To a solution of methyl 3-[(6-chloropyridazin-3-yl)methyl]-4-methoxybenzoate (10.03 g, 34.2 mmol) in THF (400 mL) was added LHMDS (100 mL, 1M solution in THF) and ethyl 3-(trimethylsilyl)propynoate (6.66 mL, 35.5 mmol) at −78° C. The reaction was warmed to 0° C. and stirred for 0.5 hr until the reaction was complete by LCMS analysis. The reaction was quenched with aqueous NH$_4$Cl and extracted with ethyl acetate. The combined organic layers were washed with 0.5 N HCl, brine, dried over MgSO$_4$, and condensed in vacuo to yield an oil. The crude material was purified via silica gel chromatography (CH$_2$Cl$_2$) to yield the title compound.

MS(ES): 417.15 (M+H).

Step-D methyl 3-(2-chloro-6-oxo-6H-pyrido[1,2-b]pyridazin-5-yl)-4-methoxybenzoate

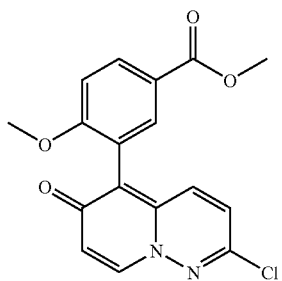

To a solution methyl 3-[1-(6-chloropyridazin-3-yl)-2-oxo-4-(trimethylsilyl)but-3-yn-1-yl]-4methoxybenzoate (5.58 g, 13.4 mmol) in THF (200 mL) was added TBAF (20.0 mL, 20 mmol) at 0° C. After 10 min the reaction was complete by TLC analysis and diluted with H$_2$O/EtOAc (1/1). The organic layer was washed with H$_2$O, brine, dried over MgSO$_4$ and concentrated to yield an oil. The crude material was dissolved in NMP (25 mL) and heated to 90° C. for 0.5 hr. The completed reaction was poured into 500 mL of ice water and the solid precipitate was collected and dried.

MS(ES): 345.16 (M+H).

Step-E methyl 3-[2-(2,4-difluorophenoxy)-6-oxo-6H-pyrido[1,2-b]pyridazin-5-yl]-4-methoxybenzoate

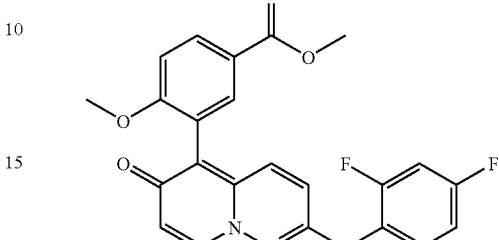

To a solution of methyl 3-(2-chloro-6-oxo-6H-pyrido[1,2-b]pyridazin-5-yl)-4-methoxybenzoate (1.05 g, 3.05 mmol) and Cs$_2$CO$_3$ (2.97 g, 9.15 mmol) dissolved in NMP (20 mL) was added 2,4 difluoro phenol (475 mg, 3.66 mmol). The mixture was heated to 80° C. for 1 hr until the reaction was complete via LCMS analysis. The reaction was poured into 500 mL of ice/H$_2$O and the solid precipitate was collected. The crude residue was purified via silica gel chromatography (EtOAc/CH$_2$Cl$_2$, MeOH) to yield the title compound.

$^1$H NMR (CDCl$_3$, 500 MHz): 8.20 (d, 1H), 8.16 (d, 1H), 7.88 (s, 1H), 7.45 (m, 2H), 7.25 (m, 2H), 7.16 (d, 1H), 7.08 (m, 1H), 6.82 (d, 1H), 3.88 (s, 3H), 3.82 (s, 3H).

MS(ES): 439.15 (M+H).

Step-F

3-[2-(2,4-difluorophenoxy)-6-oxo-6H-pyrido[1,2-b]pyridazin-5-yl]-4-methoxybenzoic acid

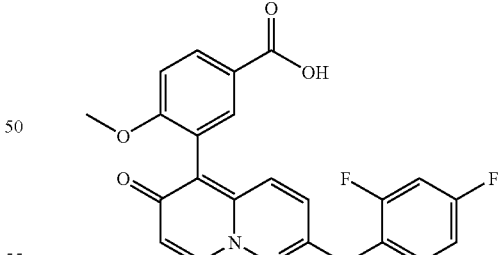

To a solution of methyl 3-[2-(2,4-difluorophenoxy)-6-oxo-6H-pyrido[1,2-b]pyridazin-5-yl]-4-methoxybenzoate (750 mg) dissolved in dioxane (10 mL) was added 1 N NaOH (10 mL). The reaction stirred at room temperature for 3 hrs until completion by LCMS analysis. The reaction was diluted with H$_2$O, washed with ether, and acidified to pH 4.5. The solid precipitate was collected and dried to yield the title compound.

MS(ES): 425.2 (M+H).

EXAMPLE-1

2-(2,4-difluorophenoxy)-5-[2-methoxy-5-(5-methyl-1,3,4-oxadiazol-2-yl)phenyl]-6H-pyrido[1,2-b]pyridazin-6-one

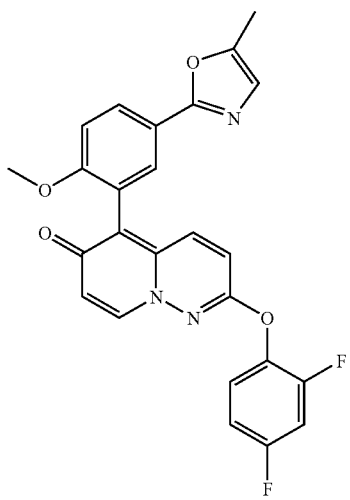

A solution of 3-[2-(2,4-difluorophenoxy)-6-oxo-6H-pyrido[1,2-b]pyridazin-5-yl]-4-methoxybenzoic acid (Intermediate 1, 424 mg, 1.0 mmol) in CH$_2$Cl$_2$ (10 mL) was added triethyl amine (202 mg, 2.0 mmol) and ethylchloroformate (162 mg, 1.8 mmol) at 0° C. The mixture was warmed to ambient temperature and stirred for 10 min. The reaction was complete by LCMS analysis and concentrated in vacuo to yield 3-[2-(2,4-difluorophenoxy)-6-oxo-6H-pyrido[1,2-b]pyridazin-5-yl]-4-methoxybenzoic propanoic anhydride.

The crude mixture was dissolved in CH$_2$Cl$_2$ and was added to a hydrazine solution (0.2 mL hydrazine in 10 mL CH$_2$Cl$_2$) via cannula. After stirring for 10 min at room temperature, the reaction was concentrated in vacuo to yield a solid. To the crude material was added trimethyl orthoacetate (3 mL) and the mixture was heated to 110° C. for 1.5 hrs. LCMS revealed the reaction was complete and the mixture was concentrated in vacuo. The crude material was purified via silica gel chromatography (CH$_2$Cl$_2$/EtOAc/MeOH) to give the title compound as a yellow solid (250 mg).

$^1$H NMR (CDCl$_3$, 500 MHz): 8.15 (d, 1H), 7.94 (s, 1H), 7.88 (d, 1H), 7.38 (d, 1H), 7.26 (m, 2H), 7.18 (d, 1H), 7.00 (m, 2H), 6.84 (d, 1H), 3.82 (s, 3H), 2.60 (s, 3H).

MS(ES): 463.4 (M+H).

EXAMPLE-2

N-cyclopropyl-3-[2-(2,4-difluorophenoxy)-6-oxo-6H-pyrido[1,2-b]pyridazin-5-yl]-4-methoxybenzamide

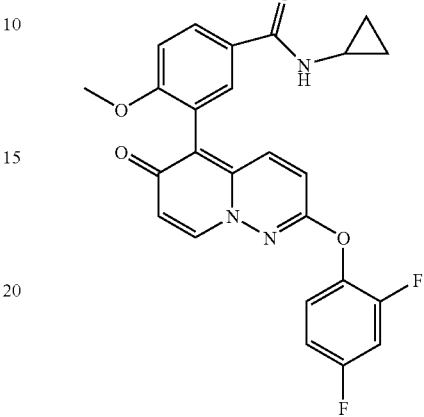

To a solution of Intermediate 1 in CH$_2$Cl$_2$ was added triethyl amine and ethylchloroformate at 0° C. The mixture was warmed to ambient temperature and stirred for 10 min. The reaction was complete by LCMS analysis and concentrated in vacuo to yield crude residue. To the crude residue was added CH$_2$Cl$_2$ and cyclopropyl amine, followed by stirring for ½ hr. LCMS indicated the reaction was complete. The reaction was diluted with CH$_2$Cl$_2$, washed with 0.5 N NaOH, H$_2$O, brine, dried over MgSO$_4$, and concentrated in vacuo. The crude residue was purified via silica gel chromatography (EtOAc/CH$_2$Cl$_2$/MeOH).

$^1$H NMR (CDCl$_3$, 500 MHz): 8.20 (d, 1H), 7.95 (d, 1H), 7.62 (s, 1H), 7.44 (m, 2H), 7.22 (m, 2H), 7.18 (d, 1H), 7.10 (m, 1H), 6.82 (d, 1H), 3.80 (s, 3H), 2.82 (m, 1H), 0.80 (m, 2H), 0.60 (m, 2H).

MS(ES): 464.1 (M+H).

EXAMPLE-3

3-[2-(2,4-difluorophenoxy)-6-oxo-6H-pyrido[1,2-b]pyridazin-5-yl]-4-methoxy-N-propylbenzamide

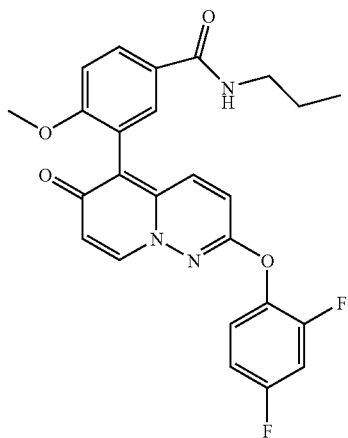

The title compound was prepared by the procedure described in Example-2 using propyl amine instead of cyclopropyl amine.

¹H NMR (CD₃OD): 8.20 (d, 1H), 7.86 (d, 1H), 7.65 (s, 1H), 7.45 (m, 2H), 7.22 (m, 2H), 7.18 (d, 1H), 7.08 (m, 1H), 6.82 (d, 1H), 3.80 (s, 3H), 3.34 (m, 2H), 1.62 (m, 2H), 0.98 (m, 3H).

MS(ES): 466.1 (M+H).

EXAMPLE-4

2-(2,4-difluorophenoxy)-5-[2-methoxy-5-(pyrrolidin-1-ylcarbonyl)phenyl]-6H-pyrido[1,2-b]pyridazin-6-one The title compound was prepared by the procedure described in Example-2 using pyrrolidine instead of cyclopropyl amine.

¹H NMR (CD₃OD): 8.18 (d, 1H), 7.68 (d, 1H), 7.50 (d, 1H), 7.44 (m, 2H), 7.22 (m, 2H), 7.15 (d, 1H), 7.08 (m, 1H), 6.82 (d, 1H), 3.80 (s, 3H), 3.55-3.64 (m, 4H), 1.90-2.02 (m, 4H).

MS(ES): 478.1 (M+H).

SCHEME 2

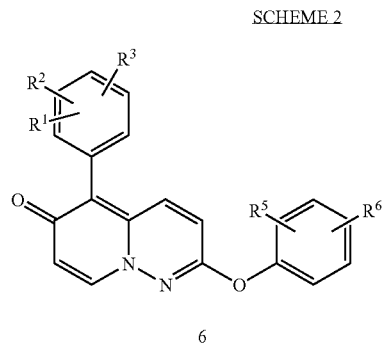

6

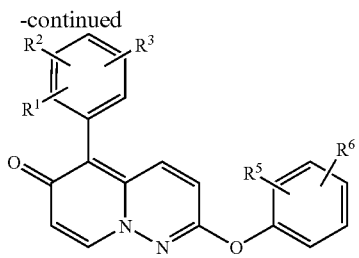

7

Compounds 6 can be converted to 7 via Pd-mediate coupling methods such as Suzuki reactions, Stille reactions or Buchward reactions.

INTERMEDIATE-2:

5-(5-bromo-2-methoxyphenyl)-2-(2,4-difluorophenoxy)-6H-pyrido[1,2-b]pyridazin-6-one

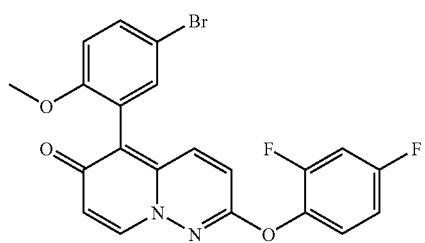

The title compound was prepared by the procedure described in Intermediate-1: Steps A-E using 5-bromo 2-methoxybenzylzinc chloride in place of bromo[2-methoxy-5-(methoxycarbonyl)benzyl]zinc.

MS(ES): 460.9 (M+H).

EXAMPLE-5

2-(2,4-difluorophenoxy)-5-(2-methoxy-5-pyrimidin-5-ylphenyl)-6H-pyrido[1,2-b]pyridazin-6-one

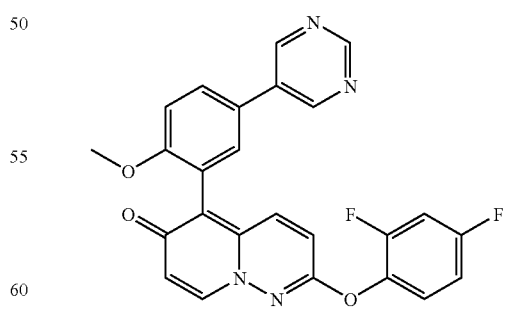

Intermediate-2 (50 mg, 0.11 mmol), pyrimidine 5-boronic acid (27.3 mg, 0.22 mmol), pd Tetrakis (12.7 mg, 0.011 mmol), toluene (2.0 mL), ethanol (0.2 mL), and 2M Na₂CO₃ (0.2 mL) were added to a flask and heated to 90° C. The reaction stirred for 16 hrs before completion by LCMS; concentration of the reaction in vacuo was followed by purification of the crude residue via silica gel chromatography (EtOAc/CH₂Cl₂/MeOH).

¹H NMR (CD₃OD): 9.06 (s, 2H), 8.22 (d, 1H), 7.84 (d, 1H), 7.62 (s, 1H), 7.58 (d, 1H), 7.45 (m, 1H), 7.36 (d, 1H), 7.22 (m, 1H), 7.18 (d, 1H), 7.08 (m, 1H), 6.84 (d, 1H), 3.82 (m, 3H).

MS(ES): 459.0 (M+H).

EXAMPLE-6

2-(2,4-difluorophenoxy)-5-(3'-fluoro-4-methoxybiphenyl-3-yl)-6H-pyrido[1,2-b]pyridazin-6-one

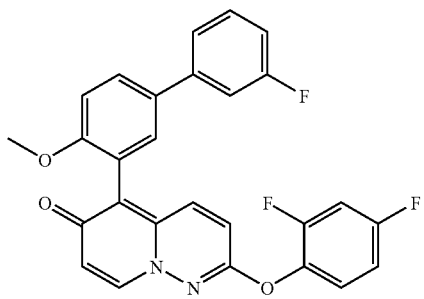

The title compound was prepared by the procedure described Example-5 using 3-F phenyl boronic acid in place of pyrimidine 5-boronic acid.

¹H NMR (CD₃OD): 8.20 (d, 1H), 7.75 (d, 1H), 7.55 (d, 1H), 7.50 (s, 1H), 7.36-7.48 (m, 4H), 7.25 (m, 2H), 7.15 (d, 1H), 7.08 (m, 1H), 7.02 (m, 1H), 6.84 (d, 1H), 3.80 (s, 3H).

MS(ES): 475.0 (M+H).

EXAMPLE-7

2-(2,4-difluorophenoxy)-5-(2-methoxy-5-vinylphenyl)-6H-pyrido[1,2-b]pyridazin-6-one

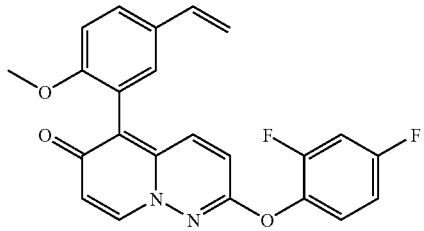

To Intermediate-2 (50 mg, 0.109) was added Tetrakis (12.6 mg, 0.0109), tributyl vinyl tin (61.2 mg, 0.163 mmol), and toluene (1.5 mL). The mixture was heated to 80° C. for 1 hr until reaction was complete by LCMS. The reaction was cooled to room temperature and 2 eq of wet DBU was added. The resulting mixture stirred overnight before the solid precipitate was filtered off. The filtrate was condensed to an oil and purified via silica gel chromatography (EtOAc/CH₂Cl₂/MeOH).

¹H NMR (CD₃OD): 8.18 (d, 1H), 7.52 (d, 1H), 7.48 (d, 1H), 7.42 (m, 1H), 7.32 (s, 1H), 7.22 (m, 1H), 7.12 (m, 3H), 6.82 (d, 1H), 6.72 (m, 1H), 5.64 (d, 1H) 5.12 (d, 1H), 3.78 (s, 3H).

MS(ES): 407.0 (M+H).

EXAMPLE-8

3-[2-(2,4-difluorophenoxy)-6-oxo-6H-pyrido[1,2-b]pyridazin-5-yl]-4-methoxybenzonitrile

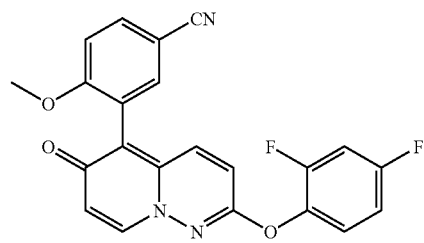

The title compound was prepared by the procedure described in Intermediate-1: Steps A-E using 5-nitrile 2-methoxybenzylzinc chloride as a starting material.

¹H NMR (CD₃OD): 8.20 (d, 1H), 7.84 (d, 1H), 7.60 (s, 1H), 7.45 (m, 2H), 7.30 (d, 1H), 7.24 (m, 1H), 7.18 (d, 1H), 7.10 (m, 1H), 6.82 (d, 1H), 3.82 (s, 3H).

MS(ES): 406.0 (M+H).

EXAMPLE-9 methyl 4-bromo-3-[2-(2,4-difluorophenoxy)-6-oxo-6H-pyrido[1,2-b]pyridazin-5-yl]benzoate

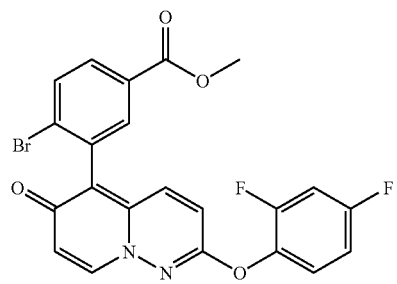

The title compound was prepared by the procedure described in Intermediate-1: Steps A-E using methyl 4-bromo-3-methylbenzoate as a starting material.

¹H NMR (CD₃OD): 8.24 (d, 1H), 8.00 (d, 1H), 7.94 (m, 2H), 7.48 (m, 1H), 7.40 (d, 1H), 7.22 (m, 2H), 7.10 (m, 1H), 6.82 (d, 1H).

MS(ES): 489.0 (M+H).

EXAMPLE-10 methyl 3-[2-(2,4-difluorophenoxy)-6-oxo-6H-pyrido[1,2-b]pyridazin-5-yl]-4-vinylbenzoate

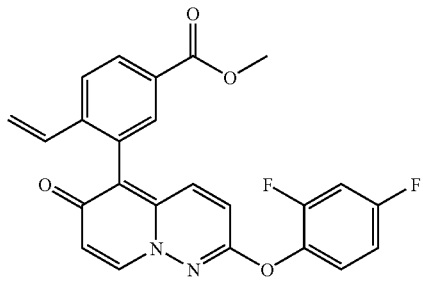

The title compound was prepared by the procedure described in Example 7 using Example 9 as a starting material.

$^1$H NMR (CD$_3$OD): 8.24 (d, 1H), 8.10 (d, 1H), 7.92 (d, 1H), 7.84 (s, 1H), 7.42 (m, 1H), 7.36 (d, 1H), 7.22 (m, 1H), 7.15 (d, 1H), 7.10 (m, 1H), 6.84 (d, 1H), 6.50 (m, 1H), 5.88 (d, 1H), 5.30 (d, 1H), 3.88 (s, 3H).

MS(ES): 435.1 (M+H).

INTERMEDIATE-3

3-[2-(2,4-difluorophenoxy)-6-oxo-6H-pyrido[1,2-b]pyridazin-5-yl]-4-vinylbenzoic acid

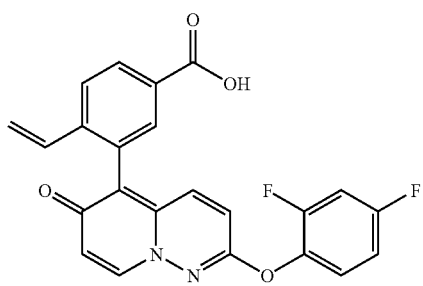

The title compound was prepared from Example-10 using the procedure described in Intermediate-1 Step-F.

MS(ES): 421.1 (M+H).

EXAMPLE-11

2-(2,4-difluorophenoxy)-5-[5-(pyrrolidin-1-ylcarbonyl)-2-vinylphenyl]-6H-pyrido[1,2-b]pyridazin-6-one

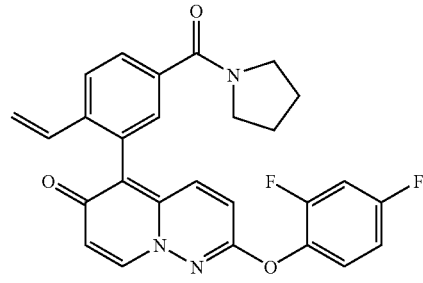

The title compound was prepared from Intermediate-3 using procedures similar to those described in Example-2.

$^1$H NMR (CD$_3$OD): 8.12 (d, 1H), 7.85 (d, 1H), 7.62 (d, 1H), 7.44 (m, 1H), 7.40 (d, 1H), 7.38 (s, 1H), 7.20 (m, 1H), 7.18 (d, 1H), 7.10 (m, 1H), 6.82 (d, 1H), 6.45 (m, 1H), 5.82 (d, 1H), 5.12 (d, 1H), 3.60 (m, 4H), 2.00 (m, 2H), 1.90 (m, 2H).

MS(ES): 474.1 (M+H).

EXAMPLE-12

N-cyclopropyl-3-[2-(2,4-difluorophenoxy)-6-oxo-6H-pyrido[1,2-b]pyridazin-5-yl]-4-vinylbenzamide

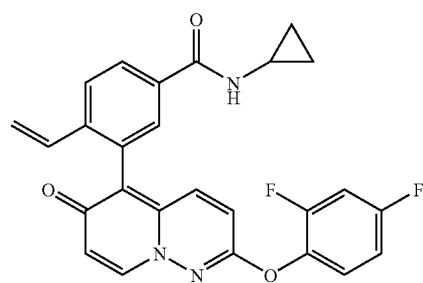

The title compound was prepared from Intermediate-3 using procedures similar to those described in Example-2.

$^1$H NMR (CD$_3$OD): 8.22 (d, 1H), 7.84 (m, 2H), 7.60 (s, 1H), 7.44 (m, 1H), 7.36 (d, 1H), 7.22 (m, 1H), 7.15 (d, 1H), 7.08 (m, 1H), 6.82 (d, 1H), 6.45 (m, 1H), 5.82 (d, 1H), 5.24 (d, 1H), 2.84 (m, 1H), 0.80 (m, 2H), 0.62 (m, 2H).

MS(ES): 460.1 (M+H).

EXAMPLE-13

3-[2-(2,4-difluorophenoxy)-6-oxo-6H-pyrido[1,2-b]pyridazin-5-yl]-N-propyl-4-vinylbenzamide

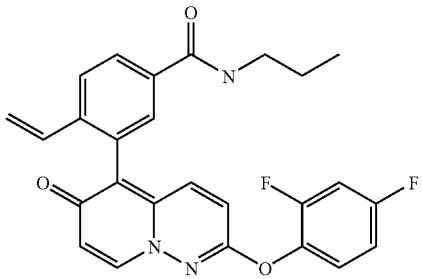

The title compound was prepared from Intermediate-3 using procedures similar to those described in Example-2.

¹H NMR (CD₃OD): 8.22 (d, 1H), 7.90 (d, 2H), 7.62 (s, 1H), 7.45 (m, 1H), 7.38 (d, 1H), 7.22 (m, 1H), 7.15 (d, 1H), 7.05 (m, 1H), 6.84 (d, 1H), 6.48 (m, 1H), 5.84 (d, 1H), 5.24 (d, 1H), 3.34 (m, 2H), 1.62 (m, 2H), 0.98 (m, 3H).

MS(ES): 462.1 (M+H).

EXAMPLE-14

2-(2,4-difluorophenoxy)-5-[2-ethyl-5-(pyrrolidin-1-ylcarbonyl)phenyl]-6H-pyrido[1,2-b]pyridazin-6-one

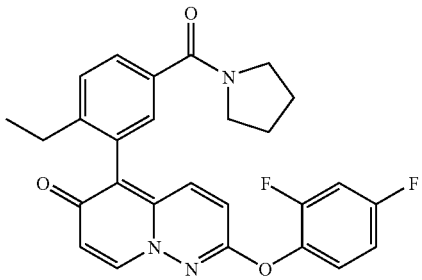

2-(2,4-difluorophenoxy)-5-[5-(pyrrolidin-1-ylcarbonyl)-2-vinylphenyl]-6H-pyrido[1,2-b]pyridazin-6-one (14 mg, 0.03 mmol) was disolved in EtOAc (2 mL) and purged with nitrogen (3×). A catalytic amount of activated Pd on carbon was added and the system was purged with nitrogen (3×) and hydrogen (3×). The reaction was complete in 30 min and the reaction was filtered through celite and concentrated. The crude residue was purified via silica gel chromatography (EtOAc/CH₂Cl₂/MeOH).

¹H NMR (CD₃OD): 8.22 (d, 1H), 7.60 (d, 1H), 7.52 (d, 1H), 7.45 (m, 2H), 7.28 (s, 1H), 7.22 (m, 1H), 7.16 (d, 1H), 7.06 (m, 1H), 6.82 (d, 1H), 3.58 (m, 4H), 2.42-2.50 (m, 2H), 1.84-2.00 (m, 4H), 1.10 (t, 3H).

MS(ES): 474.1 (M+H).

EXAMPLE-15

N-cyclopropyl-3-[2-(2,4-difluorophenoxy)-6-oxo-6H-pyrido[1,2-b]pyridazin-5-yl]-4-ethylbenzamide

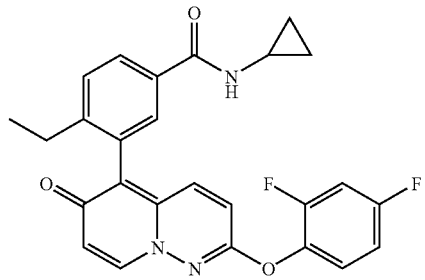

The title compound was prepared from Example-12 using procedures similar to those described in Example-14.

¹H NMR (CD₃OD): 8.20 (d, 1H), 7.84 (d, 1H), 7.52 (m, 2H), 7.45 (m, 1H), 7.40 (d, 1H), 7.24 (m, 1H), 7.15 (d, 1H), 7.08 (m, 1H), 6.82 (d, 1H), 2.82 (m, 1H), 2.42-2.52 (m, 2H), 1.08 (t, 3H), 0.78 (m, 2H), 0.60 (m, 2H).

MS(ES): 462.2 (M+H).

EXAMPLE-16

3-[2-(2,4-difluorophenoxy)-6-oxo-6H-pyrido[1,2-b]pyridazin-5-yl]-4-ethyl-N-propylbenzamide

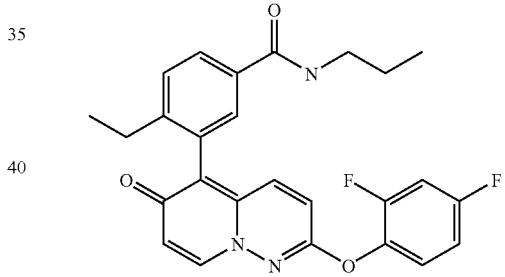

The title compound was prepared from Example-13 using procedures similar to those described in Example-14.

¹H NMR (CD₃OD): 8.24 (d, 1H), 7.88 (d, 1H), 7.54 (m, 2H), 7.46 (m, 1H), 7.42 (d, 1H), 7.24 (m, 1H), 7.15 (d, 1H), 7.10 (t, 1H), 6.84 (d, 1H), 3.32 (m, 2H), 2.42-2.52 (m, 2H), 1.62 (m, 2H), 1.08 (t, 3H), 0.45 (t, 3H).

MS(ES): 464.2 (M+H).

INTERMEDIATE-4

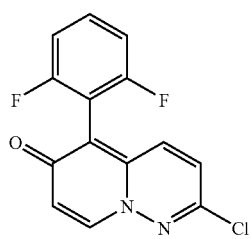

Step-A 3-chloro-6-(2,6-difluorobenzyl)pyridazine

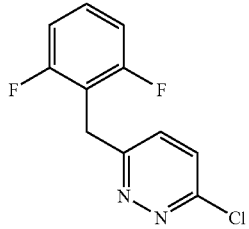

To a solution of 3,6-dichloro pyridazine (7.39 g, 50 mmol) and tetrakis(triphenylphosphine)palladium (2.89 g, 2.5 mmol) in THF (500 mL) was added 2,6 difluoro benzyl zinc bromide (120 mL, 60 mmol). The reaction mixture was heated to 80° C. for 1.5 hours until the reaction was complete by TLC. The reaction was cooled to room temperature, filtered through celite, and concentrated in vacuo. The crude residue was recrystalized from ether to yield 5.7 g of the title compound.

$^1$H NMR (CDCl$_3$): 7.42 (d, 1H), 7.18 (m, 2H), 6.96 (m, 2H), 4.42 (s, 2H,).

MS(ES): 242.9 (M+H).

Step-B 1-(6-chloropyridazin-3-yl)-1-(2,6-difluorophenyl)-4-(trimethylsilyl)but-3-yn-2-one

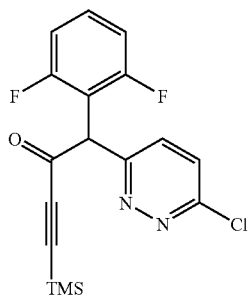

To a solution of 3-chloro-6-(2,6-difluorobenzyl)pyridazine (5.7 g, 23.7 mmol) in THF (300 mL) was added LHMDS (71.2 mL, 71.2 mmol, 1M solution in THF) via cannula at −78° C. After stirring for 0.5 hr at −78° C., ethyl 3-(trimethylsilyl)propynoate (6.66 mL, 35.5 mmol) was added. The reaction was allowed to warm from −78° C. to −10° C. over 3 hours. The reaction was known to be complete by LCMS analysis; and then quenched with aqueous NH$_4$Cl, extracted with ethyl acetate. The organic layers were combined, washed with 0.5 N HCl, water, brine, dried over MgSO$_4$, and condensed in vacuo to yield an oil. The crude material was purified via silica gel chromatography (EtOAc/Hex) to yield the title compound (9.6 g).

$^1$H NMR (CDCl$_3$): 7.40 (m, 1H), 7.28 (d, 1H), 7.02 (m, 2H), 6.88 (d, 1H), 0.02 (s, 9H).

Step-C 1-(6-chloropyridazin-3-yl)-1-(2,6-difluorophenyl)but-3-yn-2-one

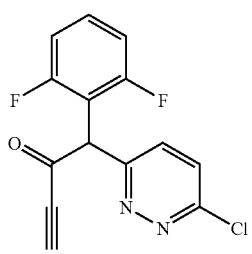

To a solution of 1-(6-chloropyridazin-3-yl)-1-(2,6-difluorophenyl)-4-(trimethylsilyl)but-3-yn-2-one (9.6 g, 26.4 mmol) in THF (200 mL) was added TBAF (32.9 mL, 32.9 mmol) at 0° C. After stirring at 0° C. for 15 min, the reaction was poured into aqueous NH$_4$Cl, and extracted with EtOAc. The combined organic layers were washed with 1N HCl, brine, dried over MgSO$_4$, and concentrated to an oil. The crude product was purified by silica gel chromatography (hexanes/CH$_2$Cl$_2$) to give title compound (10.2 g).

MS(ES): 293.1 (M+H).

Step-D 2-chloro-5-(2,6-difluorophenyl)-6H-pyrido[1,2-b]pyridazin-6-one

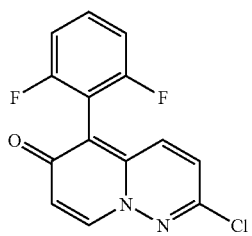

A solution of 1-(6-chloropyridazin-3-yl)-1-(2,6-difluorophenyl)but-3-yn-2-one (10.2 g) in toluene was heated to 90° C. for 3 hours. LCMS analysis revealed the reaction was complete and the reaction was concentrated to yield a solid. The crude material was purified via silica gel chromatography (CH$_2$Cl$_2$/EtOAc/MeOH) to yield the title compound.

MS(ES): 293.1 (M+H).

EXAMPLE-17

2-(2,4-difluorophenoxy)-5-(2,6-difluorophenyl)-6H-pyrido[1,2-b]pyridazin-6-one

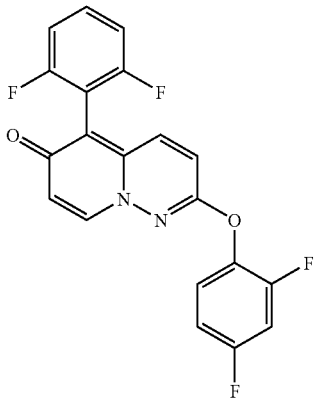

To a solution of 2-chloro-5-(2,6-difluorophenyl)-6H-pyrido[1,2-b]pyridazin-6-one (250 mg, 0.85 mmol) and $Cs_2CO_3$ (834 mg, 2.56 mmol) in NMP was added 2,4 difluoro phenol (211 mg, 1.7 mmol). The mixture was heated to 90° C. for 2 hrs until the reaction was complete via LCMS analysis. The reaction was cooled to ambient temperature and diluted with EtOAc and $H_2O$. The aqueous layer was washed with EtOAc and the combined organic layers were washed with 1N NaOH, $H_2O$, brine, dried over $MgSO_4$, and concentrated in vacuo. The crude residue was purified via silica gel chromatography (EtOAc/$CH_2Cl_2$, MeOH) to yield the title compound.

$^1$H NMR (CD$_3$OD): 8.22 (d, 1H), 7.52-7.60 (m, 2H), 7.45 (m, 1H), 7.22 (m, 2H), 7.14 (m, 2H), 7.10 (m, 1H), 6.82 (d, 1H).
MS(ES): 387.0 (M+H).

EXAMPLE-18

2-(2-chloro-4-fluorophenoxy)-5-(2,6-difluorophenyl)-6H-pyrido[1,2-b]pyridazin-6-one

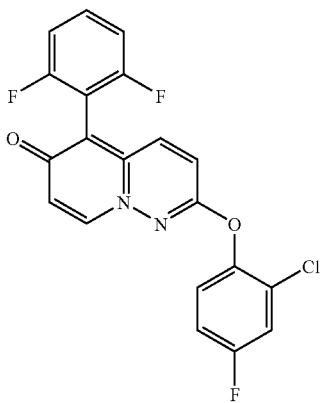

The title compound was prepared using procedures similar to those described in Example-17, substituting 2-chloro-4-fluorophenol in place of 2,4 difluorophenol.

$^1$H NMR (CD$_3$OD): 8.22 (d, 1H), 7.42-7.62 (m, 4H), 7.25 (m, 2H), 7.16 (m, 2H), 6.82 (d, 1H).
MS(ES): 403.0 (M+H).

EXAMPLE-19

2-(2,4-difluorobenzyl)-5-(2,6-difluorophenyl)-6H-pyrido[1,2-b]pyridazin-6-one

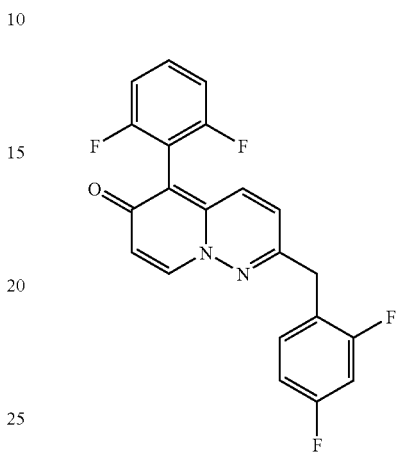

To a solution of 2-chloro-5-(2,6-difluorophenyl)-6H-pyrido[1,2-b]pyridazin-6-one (100 mg, 0.34 mmol) and Tetrakis (392 mg, 0.034 mmol) in THF was heated to 80° C. for 0.5 hrs before 2,4 difluoro benzyl zinc bromide was added. The reaction was complete after 0.5 hrs, cooled to ambient temperature, and diluted with $H_2O$ and EtOAc. The organic layer was extracted with EtOAc, $H_2O$, brine, dried over $MgSO_4$, and concentrated to a solid. The crude residue was purified via silica gel chromatography (EtOAc/$CH_2Cl_2$, MeOH) to yield the title compound.

$^1$H NMR (CD$_3$OD): 8.58 (d, 1H), 7.50 (m, 1H), 7.40 (m, 2H), 7.10 (m, 3H), 6.92-7.02 (m, 3H), 4.18 (s, 2H).
MS(ES): 385.0 (M+H).

EXAMPLE-20

5-(2,6-difluorophenyl)-2-[(2,4-difluorophenyl)amino]-6H-pyrido[1,2-b]pyridazin-6-one

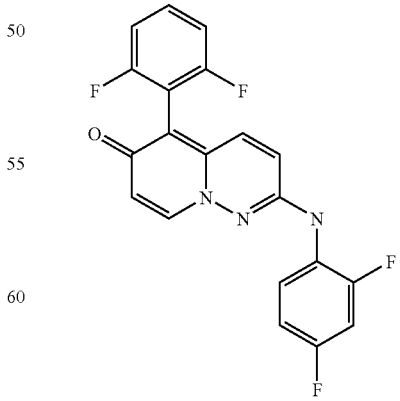

To a solution of 2-chloro-5-(2,6-difluorophenyl)-6H-pyrido[1,2-b]pyridazin-6-one (100 mg, 0.34 mmol) dissolved in toluene (1.5 mL) was added Pd(DBA) (3.1 mg, 0.0034 mmol), dppf (3.7 mg, 0.0068 mmol), sodium butoxide (23 mg, 0.238 mmol), and 2,4 difluoro aniline (43 mg, 0.34 mmol). The reaction was heated to 80° C. for 3 hours until complete by LCMS analysis. The reaction was passed through celite, condensed to an oil and purified via silica gel chromatography (EtOAc/CH$_2$Cl$_2$, MeOH) to yield the title compound.

$^1$H NMR (CD$_3$OD): 8.42 (d, 1H), 8.18 (m, 1H), 7.55 (m, 1H), 7.34 (d, 1H), 7.02-7.16 (m, 5H), 6.84 (d, 1H).

MS(ES): 386.1 (M+H).

EXAMPLE-21

5-(2,6-difluorophenyl)-2-[(2,4-difluorophenyl)thio]-6H-pyrido[1,2-b]pyridazin-6-one

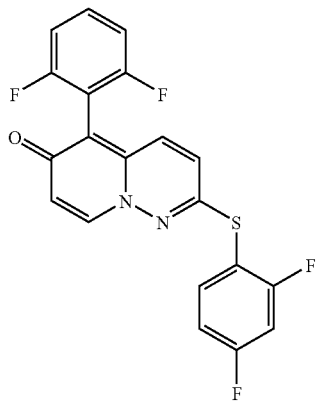

To a solution of NaH (20 mg, 0.83 mmol) and 2,4-difluorobenzenethiol (74 mg, 0.51 mmol), in THF 2 mL was added 2-chloro-5-(2,6-difluorophenyl)-6H-pyrido[1,2-b]pyridazin-6-one (50 mg, 0.17 mmol) as a solution in THF (1 mL). The reaction was complete in 10 min and concentrated in vacuo. The crude residue was purified via silica gel chromatography (EtOAc/CH$_2$Cl$_2$/MeOH) to yield the title compound.

$^1$H NMR (CD$_3$OD): 8.28 (d, 1H), 7.76 (m, 1H), 7.55 (m, 1H), 7.36 (d, 1H), 7.25 (m, 1H), 7.08-7.18 (m, 4H), 6.82 (d, 1H).

MS(ES): 402.9 (M+H).

EXAMPLE-22

2-[(2-chloro-4-fluorophenyl)thio]-5-(2,6-difluorophenyl)-6H-pyrido[1,2-b]pyridazin-6-one

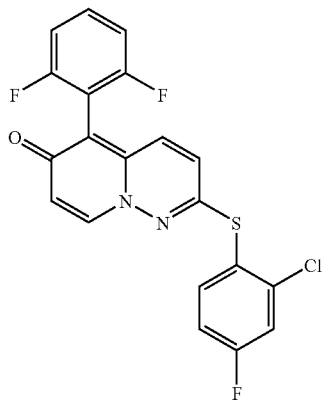

The title compound was prepared using procedures similar to those described in Example-21, substituting 2-chloro-4-fluorobenzenethiol in place of 2,4 difluorophenol.

$^1$H NMR (CD$_3$OD): 8.30 (d, 1H), 7.85 (m, 1H), 7.55 (m, 2H), 7.38 (d, 1H), 7.28 (m, 1H), 7.15 (m, 2H), 7.05 (d, 1H), 6.82 (d, 1H).

MS(ES): 418.9 (M+H).

EXAMPLE-23

2-biphenyl-2-yl-5-(2,6-difluorophenyl)-6H-pyrido[1,2-b]pyridazin-6-one

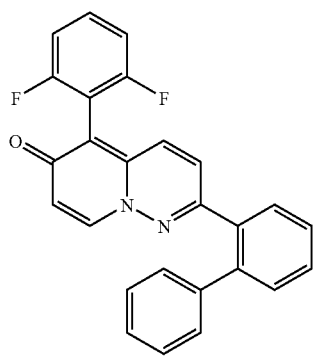

2-chloro-5-(2,6-difluorophenyl)-6H-pyrido[1,2-b]pyridazin-6-one (50 g, 0.17 mmol), biphenyl-2-ylboronic acid (51.4 mg, 0.26 mmol), and Tetrakis (19.6 g, 0.017 mmol) were added to a flask and purged with N$_2$ (3×). After the addition of toluene (5 mL), ethanol (0.5 mL), and 2M Na$_2$CO$_3$ (0.5 mL) the resulting mixture was heated to 90° C. for 1 hour. The reaction was concentrated in vacuo and the crude residue was dissolved in H$_2$O/EtOAc (1:1) and extracted with H$_2$O, 1N HCl (2×), brine (2×), dried over MgSO$_4$, and concentrated in vacuo to yield an oil. The crude material was purified via silica gel chromatography (CH$_2$Cl$_2$/EtOAc/MeOH) to yield the title compound.

$^1$H NMR (CD$_3$OD): 1H NMR (CD$_3$OD) δ: 8.64 (d, 1H), 7.80 (d, 1H), 7.64 (m, 1H), 7.55 (m, 2H), 7.50 (m, 1H), 7.36 (m, 3H), 7.18 (m, 2H), 7.08 (m, 3H), 6.98 (d, 1H), 6.64 (d, 1H).

MS(ES): 411.1 (M+H).

Scheme 3
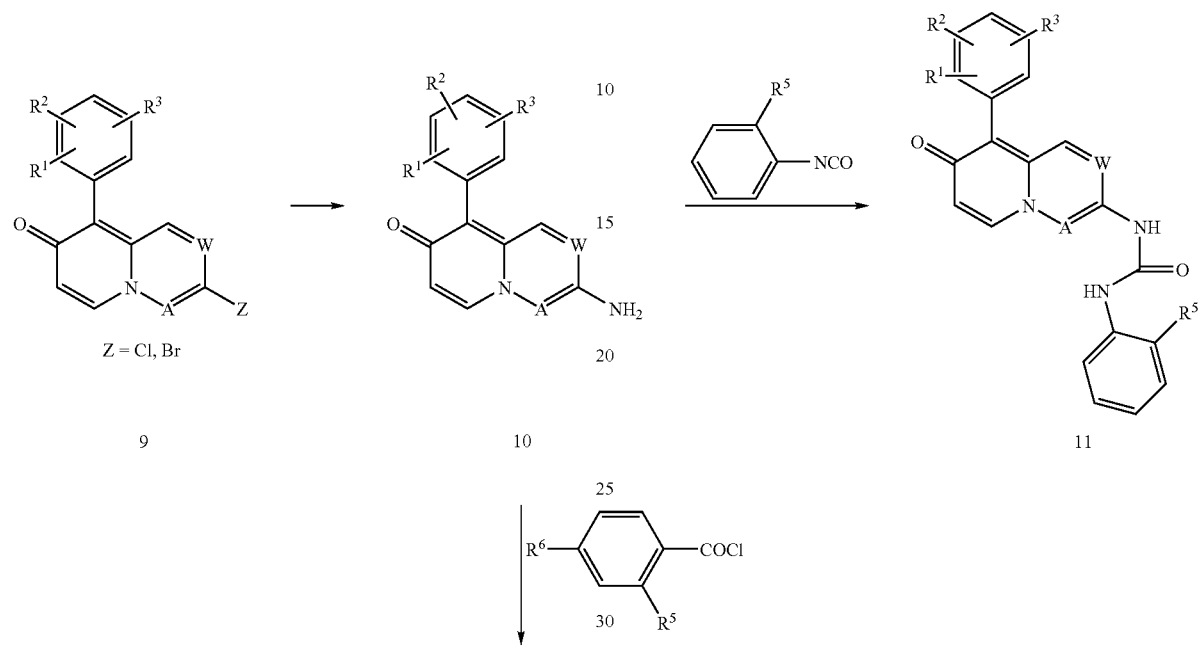
9 10 11
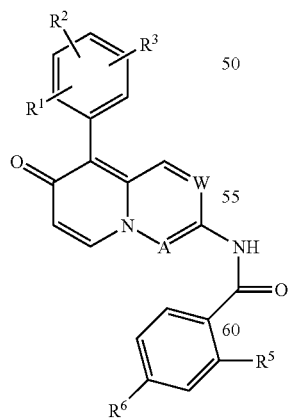
12

Compounds 9 can be converted to compounds 10 using known methods such as substitution reactions. The amino analogs 10 can further be converted to amides 12 or ureas 11 by standard peptide coupling conditions or reacting with isocyanate.

INTERMEDIATE-5

2-amino-5-(2,6-difluorophenyl)-6H-pyrido[1,2-b]pyridazin-6-one

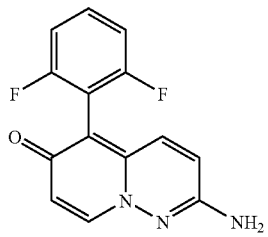

To 2-chloro-5-(2,6-difluorophenyl)-6H-pyrido[1,2-b]pyridazin-6-one (1.1 g, 3.77 mmol) was added NH$_4$Cl (100 mL) and NH$_4$OH (100 mL). The resulting solution was heated to 90° C. and stirred for 16 hrs until complete. The reaction was cooled to ambient temperature and diluted with H$_2$O (500 mL) until a precipitate formed. The solid precipitate was collected and dried to yield the title compound.

MS(ES): 274.1 (M+H).

EXAMPLE-24

N-[5-(2,6-difluorophenyl)-6-oxo-6H-pyrido[1,2-b]pyridazin-2-yl]-N'-(2-fluorophenyl)urea

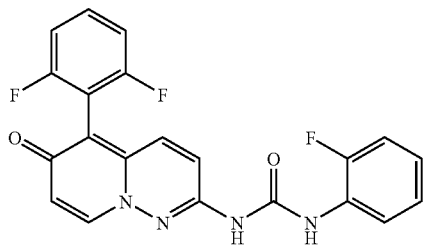

2-amino-5-(2,6-difluorophenyl)-6H-pyrido[1,2-b]pyridazin-6-one (50 mg, 0.18 mmol), toluene (3 mL), triethyl amine (36 mg, 0.36 mmol), and 1-fluoro-2-isocyanatobenzene (49 mg, 0.36 mmol) were added to a flask and heated to reflux. The reaction was complete in 3 hrs and concentrated to dryness. The crude residue was purified via silica gel chromatography (CH$_2$Cl$_2$/EtOAc/MeOH) to yield the title compound.

MS(ES): 411.1 (M+H).

EXAMPLE-25

N-[5-(2,6-difluorophenyl)-6-oxo-6H-pyrido[1,2-b]pyridazin-2-yl]-2,4-difluorobenzamide

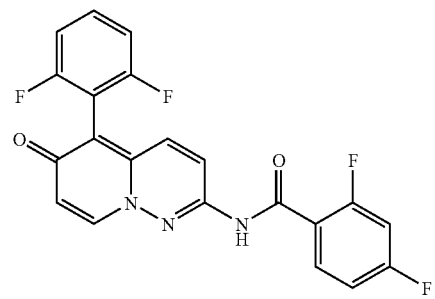

To a solution of 2-amino-5-(2,6-difluorophenyl)-6H-pyrido[1,2-b]pyridazin-6-one (50 mg, 0.18 mmol) dissolved in dichloroethane (2 mL) was added triethyl amine (0.079 mL, 0.55 mmol) and 2,4-difluorobenzoyl chloride (49 mg, 0.28 mmol). The mixture was heated to 80° C. for 2 hrs until no further progress was observed. Concentrated reaction to an oil and the crude residue was purified via silica gel chromatography (CH$_2$Cl$_2$/MeOH) to yield the title compound.

MS(ES): 414.0 (M+H).

EXAMPLE-26

2-(2,4-difluorophenoxy)-5-(3-methoxyphenyl)-6H-pyrido[1,2-b]pyridazin-6-one

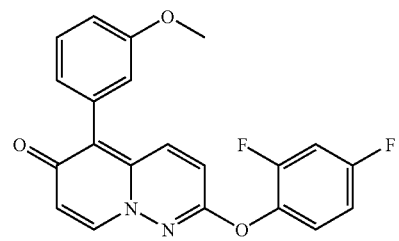

The title compound was prepared using procedures similar to those described in Example 17 and Intermediate 4, substituting 3-methoxybenzylzinc chloride solution in place of 2,6 difluorobenzylzinc bromide in Step A of Intermediate 4.

$^1$H NMR (CD$_3$OD): 8.18 (d, 1H), 7.68 (d, 1H), 7.42 (m, 2H), 7.24 (m, 1H), 7.15 (d, 1H), 7.08 (m, 1H), 7.02 (d, 1H), 6.88 (m, 2H), 6.82 (d, 1H), 3.82 (s, 3H).

MS(ES): 381.0 (M+H).

EXAMPLE-27

2-(2,4-difluorophenoxy)-5-(2-methoxyphenyl)-6H-pyrido[1,2-b]pyridazin-6-one

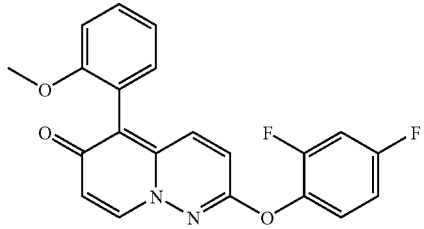

The title compound was prepared using procedures similar to those described in Example 17 and Intermediate 4, substituting 2-methoxybenzylzinc chloride solution in place of 2,6 difluorobenzylzinc chloride for Step A of Intermediate 4.

¹H NMR (CD₃OD): 8.18 (d, 1H), 7.45 (m, 3H), 7.22 (m, 2H), 7.05-7.18 (m, 4H), 6.82 (d, 1H), 3.75 (s, 3H).

MS(ES): 381.0 (M+H).

EXAMPLE-28

2-(2,4-difluorophenoxy)-5-(2-fluorophenyl)-6H-pyrido[1,2-b]pyridazin-6-one

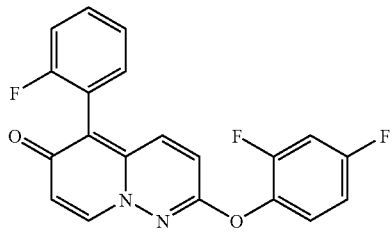

The title compound was prepared using procedures similar to those described in Example 17 and Intermediate 4, substituting 2-fluorobenzylzinc chloride solution in place of 2,6 difluorobenzylzinc chloride in Step A of Intermediate 4.

¹H NMR (CD₃OD): 8.12 (d, 1H), 7.58 (d, 1H), 7.42-7.52 (m, 2H), 7.35 (m, 2H), 7.20-7.30 (m, 3H), 7.08 (m, 1H), 6.82 (d, 1H).

EXAMPLE-29

5-(2-bromophenyl)-2-(2,4-difluorophenoxy)-6H-pyrido[1,2-b]pyridazin-6-one

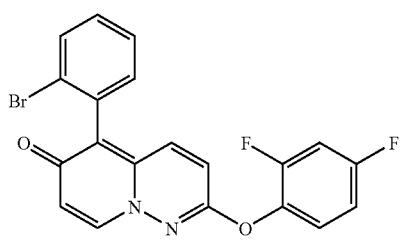

The title compound was prepared using procedures similar to those described in Example 17 and Intermediate 4, substituting 2-bromobenzylzinc chloride solution in place of 2,6 difluorobenzylzinc chloride in Step A of Intermediate 4.

¹H NMR (CD₃OD): 8.22 (d, 1H), 7.80 (d, 1H), 7.15-7.52 (m, 5H), 7.22 (m, 2H), 7.08 (m, 1H), 6.82 (d, 1H).

MS(ES): 430.8 (M+H).

EXAMPLE-30

2-(2,4-difluorophenoxy)-5-(2-vinylphenyl)-6H-pyrido[1,2-b]pyridazin-6-one

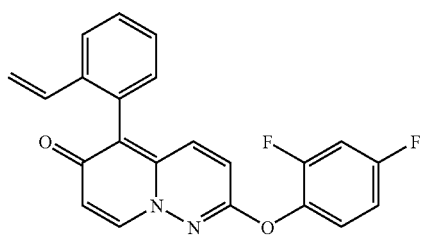

The title compound was prepared using procedures similar to those described in Example 7, using 5-(2-bromophenyl)-2-(2,4-difluorophenoxy)-6H-pyrido[1,2-b]pyridazin-6-one.

¹H NMR (CD₃OD): 8.22 (d, 1H), 7.78 (d, 1H), 7.40-7.50 (m, 3H), 7.34 (d, 1H), 7.20 (m, 2H), 7.10 (m, 2H), 6.82 (d, 1H), 6.45 (m, 1H), 5.72 (d, 1H), 5.15 (d, 1H).

MS(ES): 377.0 (M+H).

EXAMPLE-31

2-(2,4-difluorophenoxy)-5-(2-ethylphenyl)-6H-pyrido[1,2-b]pyridazin-6-one

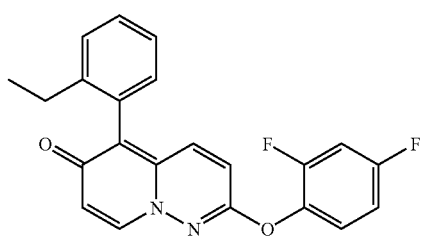

The title compound was prepared from Example 30 using procedures similar to those described in Example 14.

¹H NMR (CD₃OD): 8.22 (d, 1H), 7.38-7.50 (m, 4H), 7.34 (m, 1H), 7.24 (m, 1H), 7.10 (m, 3H), 6.82 (d, 1H), 2.44 (m, 2H), 1.05 (t, 3H).

MS(ES): 379.1 (M+H).

EXAMPLE-32

2-(2,4-difluorophenoxy)-5-[2-(2-furyl)phenyl]-6H-pyrido[1,2-b]pyridazin-6-one

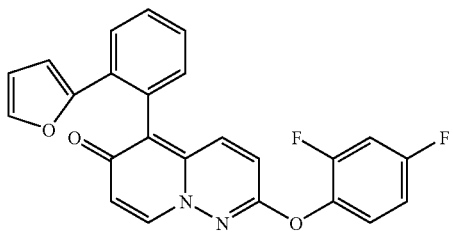

The title compound was prepared from 5-(2-bromophenyl)-2-(2,4-difluorophenoxy)-6H-pyrido[1,2-b]pyridazin-6-one as described in Example-7 using tri-N-butyl(2-furyl)tin in place of tri-N-butyl (vinyl)tin.

$^1$H NMR (CD$_3$OD): 8.22 (d, 1H), 7.90 (d, 1H), 7.54 (t, 1H), 7.45 (m, 2H), 7.38 (m, 2H), 7.24 (m, 2H), 7.05 (m, 2H), 6.82 (d, 1H), 6.30 (m, 1H), 6.08 (m, 1H).

MS(ES): 417.1 (M+H).

EXAMPLE-33

2-(2,4-difluorophenoxy)-5-{2-[(1E)-prop-1-en-1-yl]phenyl}-6H-pyrido[1,2-b]pyridazin-6-one

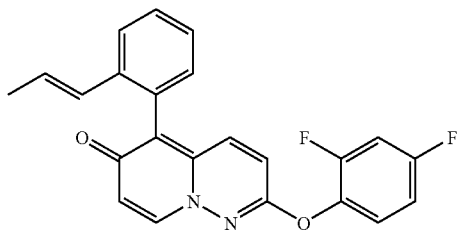

The title compound was prepared from 5-(2-bromophenyl)-2-(2,4-difluorophenoxy)-6H-pyrido[1,2-b]pyridazin-6-one as described in Example-7 using tri-N-butyl(1-propenyl)tin in place of tri-N-butyl (vinyl)tin. 50/50 mixture of cis and trans.

MS(ES): 391.1 (M+H).

EXAMPLE-34

2-(2,4-difluorophenoxy)-5-(2-propylphenyl)-6H-pyrido[1,2-b]pyridazin-6-one

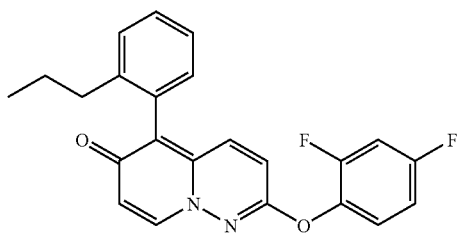

The title compound was prepared from Example-33 using procedures similar to those described in Example-14.

$^1$H NMR (CD$_3$OD): 8.22 (d, 1H), 7.40-7.48 (m, 4H), 7.35 (m, 1H), 7.22 (m, 1H), 7.10 (m, 3H), 6.82 (d, 1H), 2.40 (t, 2H), 1.40-1.50 (m, 2H), 0.80 (t, 3H). MS(ES): 393.0 (M+H).

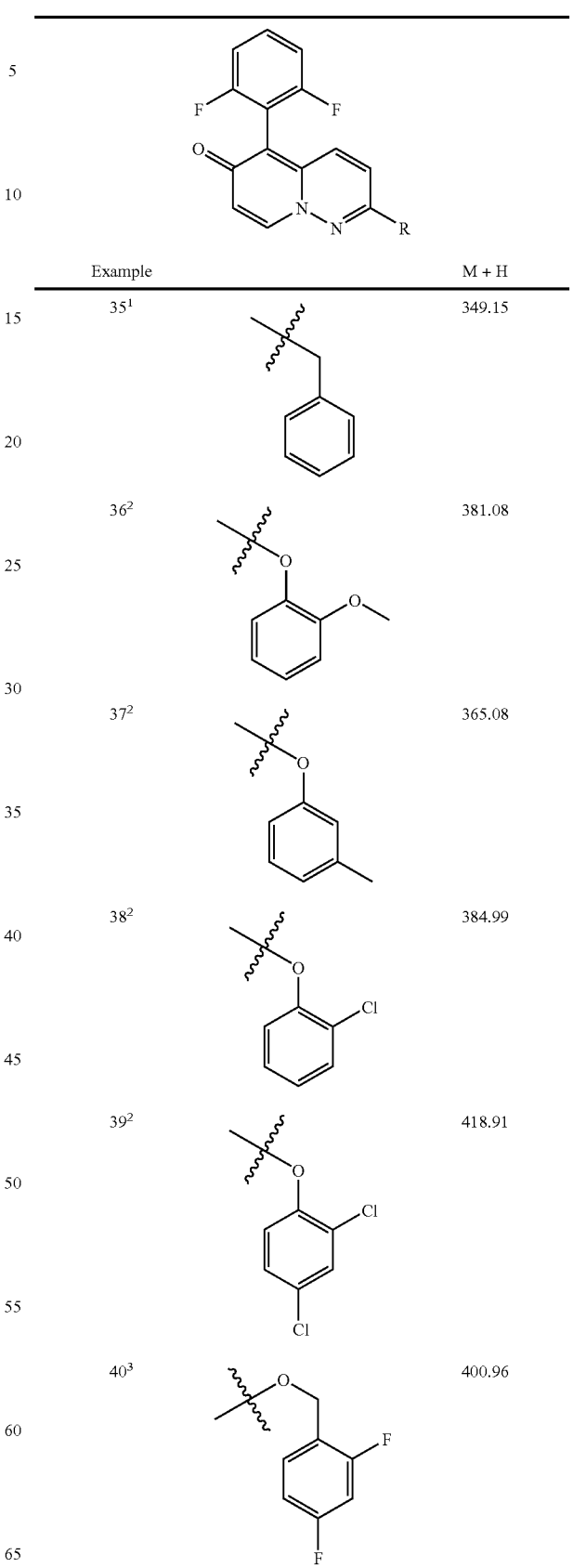

-continued

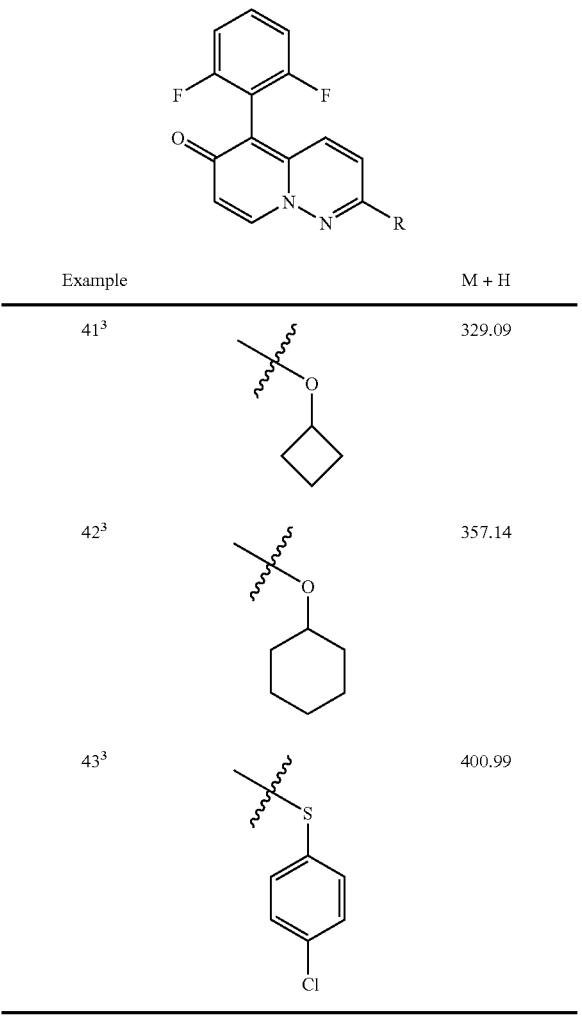

| Example | | M + H |
|---|---|---|
| 41[3] | | 329.09 |
| 42[3] | | 357.14 |
| 43[3] | | 400.99 |

[1] The title compound was prepared from Intermediate-4 as described in Example-14.
[2] The title compound was prepared from Intermediate-4 as described in Example-17.
[3] The title compound was prepared from Intermediate-4 as described in Example-21.

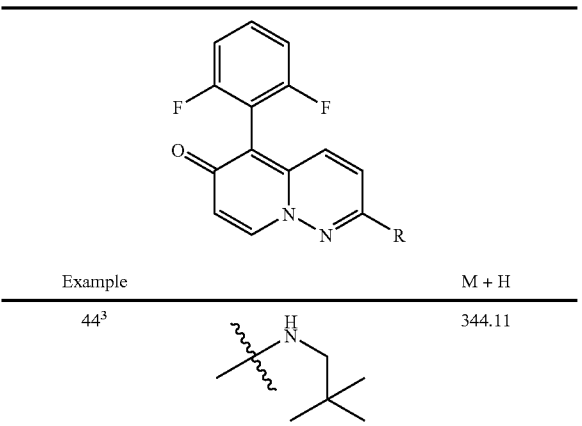

| Example | | M + H |
|---|---|---|
| 44[3] | | 344.11 |

-continued

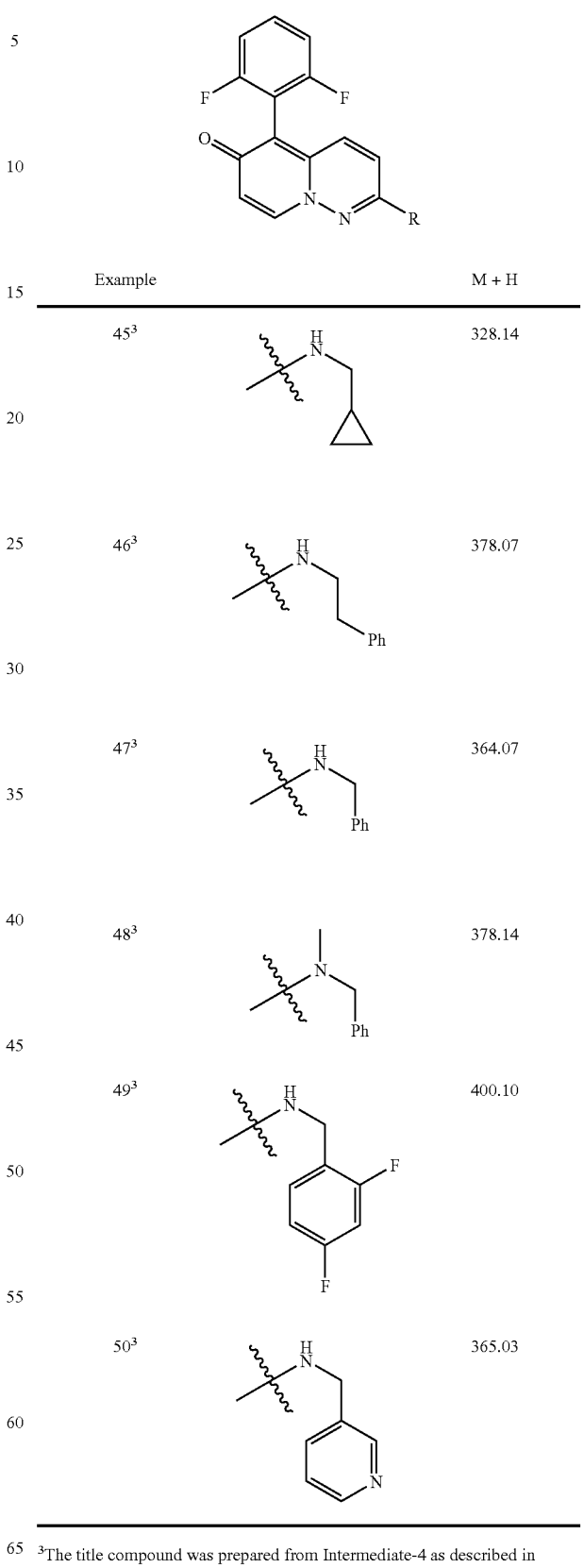

| Example | | M + H |
|---|---|---|
| 45[3] | | 328.14 |
| 46[3] | | 378.07 |
| 47[3] | | 364.07 |
| 48[3] | | 378.14 |
| 49[3] | | 400.10 |
| 50[3] | | 365.03 |

[3] The title compound was prepared from Intermediate-4 as described in Example-21.

INTERMEDIATE-6

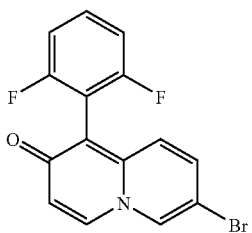

Step-A 5-bromo-2-(2,6-difluorobenzyl)pyridine

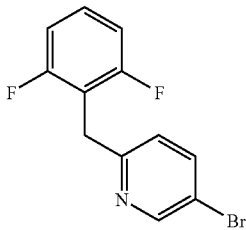

To a solution of 2,5-dibromopyridine (10 g) in THF was added Tetrakis (2.2 g) and 2,6-difluorobenzylzinc bromide (126 mL, 63 mmol). The reaction was heated to reflux until reaction was complete by TLC. The reaction was cooled to room temperature, filtered through celite, and concentrated in vacuo. The title compound was purified by silica gel (Hexanes/methylene chloride).

$^1$H NMR (CDCl$_3$): 8.60 (d, 1H), 7.72 (dd, 1H), 7.24 (m, 1H), 7.07 (d, 1H), 6.93 (m, 2H), 4.19 (s, 2H).

Step-B 1-(5-bromopyridin-2-yl)-1-(2,6-difluorophenyl)-4-(trimethylsilyl)but-3-yn-2-one

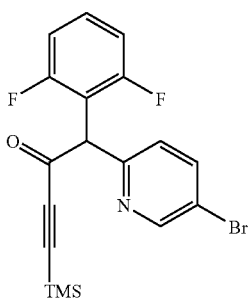

To a solution of 5-bromo-2-(2,6-difluorobenzyl)pyridine (5.6 g) in THF was added ethyl 3-(trimethylsily)propynoate (4.2 mL) and LHMD (42 mL, 1N in THF) at −78° C. The mixture was warmed to 0° C. and stirred in additional 2 h. The reaction was complete by TLC and quenched with NH$_4$Cl, extracted with ethyl acetate. The organic layer was washed with water, brine, dried over MgSO$_4$ and condensed in vacuo. The crude compound was purified by silica gel (hexanes/methylene chloride) to give the desired product.

MS(ES): 410.0 (M+H).

Step-C 1-(5-bromopyridin-2-yl)-1-(2,6-difluorophenyl)but-3-yn-2-one

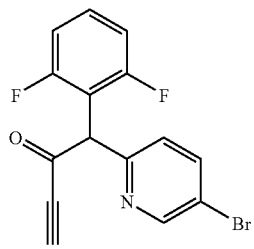

To a solution of 1-(5-bromopyridin-2-yl)-1-(2,6-difluorophenyl)-4-(trimethylsilyl)but-3-yn-2-one (4.1 g) in THF was added TBAF (12 mL, 1N in THF) at 0° C. After stirring at 0° C. for 15 min, the reaction was poured into aqueous NH$_4$Cl, and extracted with EtOAc. The combined organic layers were washed with water, brine, dried over MgSO$_4$, and concentrated to an oil. The crude product was purified by silica gel chromatography (CH$_2$Cl$_2$) to give the title compound.

MS(ES): 338.1 (M+H).

Step-D 7-bromo-1-(2,6-difluorophenyl)-2H-quinolizin-2-one

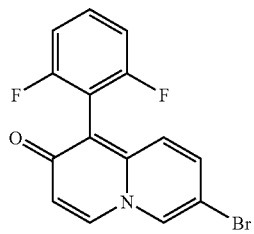

To a solution of 1-(5-bromopyridin-2-yl)-1-(2,6-difluorophenyl)but-3-yn-2-one (2 g) in TMEDA was heated to 90° C. for 1 h. LCMS analysis revealed the reaction was complete and the reaction was concentrated. The crude material was purified by silica gel chromatography (CH$_2$Cl$_2$/acetone) to yield the title compound.

$^1$H NMR (CDCl$_3$): 7.81 (s, 1H), 7.78 (d, 1H), 7.40 (m, 1H), 7.04 (m, 3H), 6.92 (d, 1H), 6.83 (d, 1H).

MS(ES): 338.0 (M+H).

EXAMPLE 51

7-(2,4-difluorophenoxy)-1-(2,6-difluorophenyl)-2H-quinolizin-2-one

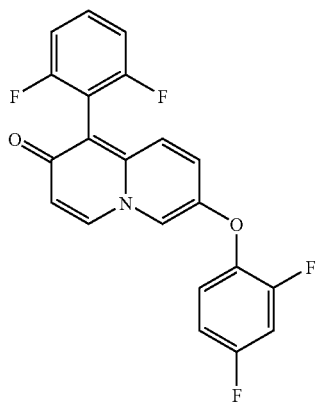

To a solution of 7-bromo-1-(2,6-difluorophenyl)-2H-quinolizin-2-one (100 mg, 0.3 mmole) was added 2,4-difluorophenol (0.06 ml, 0.6 mmole), 2,2,6,6-tetramethylheptane-3,5-dione (0.007 ml, 0.03 mmole), CuCl (15 mg, 0.15 mmole) and cesium carbonate (195 mg, 0.6 mmole) in NMP. The mixture was heated to 120° C. until the reaction completed. The mixture was diluted with ethyl acetate, washed with 1N HCl, 1N NaOH, brine, dried over MgSO$_4$, and concentrated to yield crude material. The crude material was purified by silica gel chromatography (CH$_2$Cl$_2$/acetone) to yield the title compound.

MS(ES): 386.1 (M+H).

EXAMPLE 52

1-(2,6-difluorophenyl)-7-[(2,4-difluorophenyl)thio]-2H-quinolizin-2-one

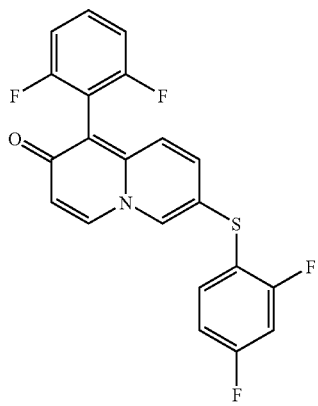

The title compound was prepared using procedures similar to those described in Example 51, using 2,4-difluorothiophenon instead of 2,4-difluorophenol.

$^1$H NMR (CDCl$_3$): 7.83 (d, 1H), 7.81 (d, 1H), 7.45 (m, 1H), 7.37 (m, 1H), 7.01 (m, 2H), 6.92 (m, 4H), 6.86 (d, 1H).

MS(ES): 402.0 (M+H).

EXAMPLE 53

7-(2,4-difluorobenzyl)-1-(2,6-difluorophenyl)-2H-quinolizin-2-one

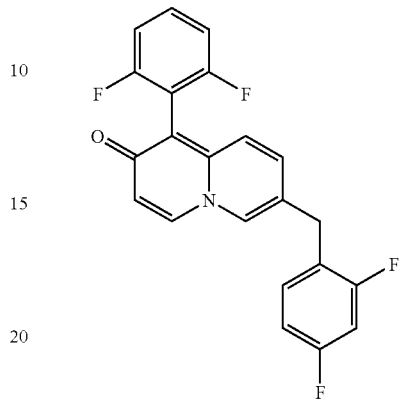

To a solution of 7-bromo-1-(2,6-difluorophenyl)-2H-quinolizin-2-one (100 mg, 0.3 mmole) was added 2,4-difluorobenzylzincbromide (0.5 N in THF, 1.2 ml), and tetrakis (15 mg) in THF. The mixture was heated to 90° C. until reaction complete. The mixture was diluted with ethyl acetate, washed with 1N HCl, brine and dried over MgSO$_4$. Upon concentration, the mixture was purified by gel chromatography (100% ethyl acetate) to yield the title compound.

$^1$H NMR (CDCl$_3$): 7.81 (d, 1H), 7.46 (s, 1H), 7.36 (m, 1H), 7.18 (m, 1H), 7.01 (m, 2H), 6.89 (m, 5H), 3.83 (s, 2H).

MS(ES): 384.1 (M+H).

EXAMPLE 54

1-(2,6-difluorophenyl)-7-[(2,4-difluorophenyl)ethynyl]-2H-quinolizin-2-one

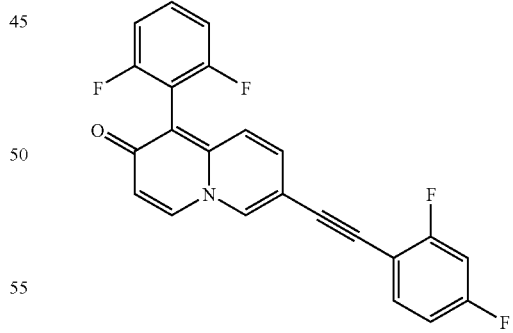

To a solution of 7-bromo-1-(2,6-difluorophenyl)-2H-quinolizin-2-one (100 mg) was added 1ethynyl-2,4-difluorobenzene (82 mg), triethylamine (0.17 ml), dichlorobis(triphenylphosphine)palladium (25 mg), CuI (6 mg) in DMF was heated to 100° C. until reaction complete. The mixture was diluted with ethyl acetate, washed with water (4×), brine, dried over MgSO$_4$, and concentrated to yield crude material. The crude material was purified by silica gel chromatography (100% ethyl acetate) to yield the title compound.

53

¹H NMR (CDCl₃): 7.88 (s, 1H), 7.83 (d, 1H), 7.51 (m, 1H), 7.36 (m, 1H), 7.41 (m, 1H), 7.08 (m, 3H), 6.94 (m, 4H).

EXAMPLE 55

1-(2,6-difluorophenyl)-7-[(Z)-2-(2,4-difluorophenyl)vinyl]-2H-quinolizin-2-one

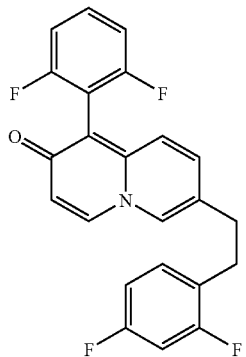

A solution of 1-(2,6-difluorophenyl)-7-[(2,4-difluorophenyl)ethynyl]-2H-quinolizin-2-one in methanol was added a catalytic amount of Lindlar catalyst under hydrogen atmosphere (1 atm) for 1 hour. The mixture was filtered through celite and the filtrate was concentrated. The crude material was purified by silica gel (100% ethyl acetate) to give the title compound.

MS(ES): 396.1 (M+H).

EXAMPLE 56

1-(2,6-difluorophenyl)-7-[2-(2,4-difluorophenyl)ethyl]-2H-quinolizin-2-one

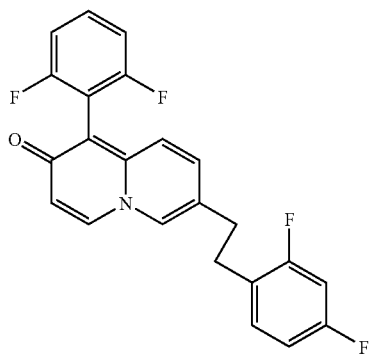

A solution of 1-(2,6-difluorophenyl)-7-[(2,4-difluorophenyl)ethynyl]-2H-quinolizin-2-one in methanol was added a catalytic amount of Pd/C under hydrogen atmosphere (1 atm) for 1 hour. The mixture was filtered through celite and the filtrate was concentrated. The crude material was purified by silica gel (100% ethyl acetate) to give the title compound.

¹H NMR (CDCl₃): 7.77 (d, 1H), 7.37 (m, 2H), 7.10 (m, 1H), 7.04 (m, 2H), 6.91 (m, 3H), 6.83 (m, 2H), 2.92 (m, 2H), 2.79 (m, 2H).

EXAMPLE 57

2-(2,4-difluorophenoxy)-5-[2-fluoro-5-(5-methyl-1,3,4-oxadiazol-2-yl)phenyl]-6H-pyrido[1,2-b]pyridazin-6-one

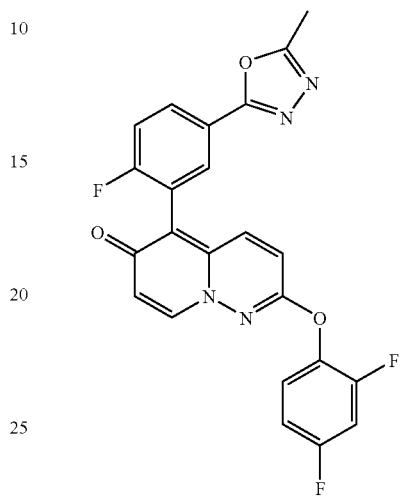

The title compound was prepared by the procedures described in Intermediate 1 and Example 1 by using methyl 4-fluoro-3-methylbenzoate as a starting material.

¹H NMR (CDCl₃) δ : 8.14 (m, 1H), 8.08 (m, 1H), 7.89 (d, 1H), 7.44 (dd, 1H), 7.36 (t, 1H), 7.26 (m, 1H), 7.03 (m, 1H), 6.99 (m, 1H), 6.91 (d, 1H), 6.84 (d, 1H), 2.61 (s, 3H). MS(ES): 451.3 (M+H).

What is claimed is:

1. A compound represented by chemical formula (I)

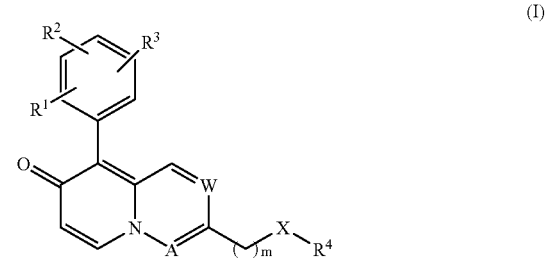

or a pharmaceutically acceptable salt thereof, wherein:

X is a single covalent bond is selected from the group consisting of:
(1) O,
(2) $C_1$-$C_4$ alkylene,
(3) $S(O)_n$,
(4) $C_2$-$C_6$ alkenylene,
(5) C(O),
(6) CHR$^a$, (7)

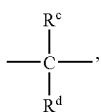

(8) NR$^a$,
(9) arylene, and
(10) heteroarylene, said arylene and heteroarylene are each optionally substituted with one or more substituents selected from R$^5$ and R$^6$;

R$^a$ is selected from the group consisting of:
(1) hydrogen,
(2) C$_1$-C$_6$ alkyl,
(3) C$_1$-C$_6$ alkoxy,
(4) CONH$_2$,
(5) C(O)$_2$R$^4$,
(6) C$_0$-C$_4$alkyl-OH,
(7) O—C$_1$-C$_4$ alkyl,
(8) halogen,
(9) aryl,
(10) heteroaryl,
(11) heterocycloalkyl,
(12) COR$^4$,
(13) N(R$^4$)(R$^4$),
(14) O—R$^4$,
(15) N—C$_1$-C$_4$alkyl-O—R$^4$;

said heteroaryl and aryl are each optionally substituted with one or more substituents selected from R$^5$ and R$^6$;

R$^c$ and R$^d$ are each independently selected from hydrogen, C$_1$-C$_6$ alkyl, C$_1$-C$_6$ alkoxy, and O—C$_1$-C$_6$ alkyl, or R$^c$ and R$^d$ can join together with the carbon atom to which they are attached to form a ring selected from the group consisting of cycloalkyl and heterocycloalkyl;

R$^1$, R$^2$ and R$^3$ are each independently selected from the group consisting of:
(1) hydrogen,
(2) C$_1$-C$_6$ alkoxy,
(3) C$_3$-C$_6$ cycloalkyl,
(4) heteroaryl,
(5) CN,
(6) halogen,
(7) C$_1$-C$_6$ alkyl,
(8) C$_2$-C$_6$ alkene,
(9)

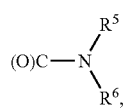

(10) C(O)—R$^4$,
(11) aryl,
(12) OR$^4$,
(13) CON(R$^4$)$_2$,
(14) N(R$^4$)$_2$,
(15) C$_1$-C$_4$—OH,
(16) heterocycloalkyl,
(17) C(O)$_2$—R$^4$ said aryl, heteroaryl, heterocycloalkyl, and cycloalkyl are each optionally substituted with one or more substituents selected from R$^5$ and R$^6$;

R$^4$ is selected from the group consisting of:
(1) aryl,
(2) hydrogen,
(3) halogen,
(4) heteroaryl,
(5) C$_1$-C$_6$ alkyl-aryl,
(6) C$_3$-C$_6$ cycloalkyl,
(7) C$_1$-C$_6$ alkyl,
(8) C$_1$-C$_6$ alkyl-C$_3$-C$_6$ cycloalkyl,
(9) C$_1$-C$_6$ alkyl-heteroaryl,
(10)

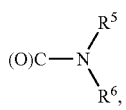

(11) C(O)—R$^5$,
(12) NH—C$_1$-C$_4$ alkyl,
(13) NH-aryl,
(14) C$_1$-C$_4$ alkyl-heterocycloalkyl,
(15) heterocycloalkyl,
(16) C$_0$-C$_4$alkyl-NH$_2$, and
(17) C$_0$-C$_4$alkyl-OH;

said heteroaryl, aryl, heterocycloalkyl and cycloalkyl are each optionally substituted with one or more substituents selected from R$^5$ and R$^6$;

R$^5$ and R$^6$ are each independently selected from:
(1) hydrogen,
(2) halogen,
(3) C$_1$-C$_6$ alkoxy,
(4) aryl,
(5) C$_3$-C$_6$ cycloalkyl,
(6) C$_1$-C$_6$ alkyl, and
(7) heteroaryl, said heteroaryl and aryl are each optionally substituted with one or more substituents selected from R$^7$, or R$^5$ and R$^6$, together with the nitrogen atom to which they are attached, can join to form a 5- to 7-membered heteroaryl or heterocycloalkyl R$^7$ is selected from the group consisting of:
(1) hydrogen,
(2) halogen,
(3) aryl,
(4) C$_3$-C$_6$ cycloalkyl,
(5) NH—C$_1$-C$_4$ alkyl,
(6) C$_1$-C$_6$ alkyl,
(7) heteroaryl,
(8) C$_1$-C$_4$alkyl-heterocycloalkyl,
(9) heterocycloalkyl,
(10) C$_0$-C$_4$alkyl-NH$_2$, and
(11) C$_0$-C$_4$alkyl-OH;

m is 0, 1, 2, or 3; and
n is 0, 1, or 2.

2. The compound according to claim 1 represented by the chemical Formula Ib, or a pharmaceutically acceptable salt thereof:

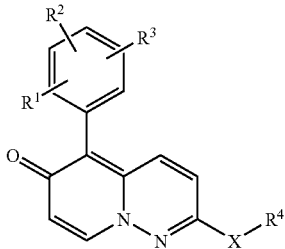
(Ib)

wherein all variables are as defined in Formula I.

3. The compound according to claim 1 represented by the chemical Formula Ic, or a pharmaceutically acceptable salt thereof:

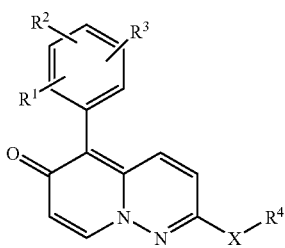
(Ic)

wherein $R^1$, $R^2$, $R^3$, and $R^4$ are as defined in Formula I, and X is selected from $CH_2$ and O.

4. The compound according to claim 1 represented by the chemical Formula Id, or a pharmaceutically acceptable salt thereof:

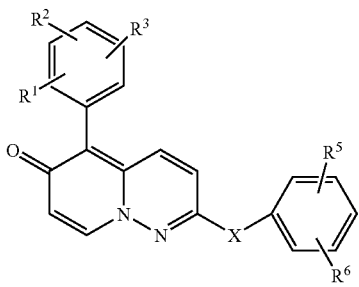
(Id)

wherein $R^1$, $R^2$, $R^3$, $R^5$ and $R^6$ are as defined in Formula I, and X is selected from $CH_2$ and O.

5. The compound according to claim 1 represented by the chemical Formula Ie, or a pharmaceutically acceptable salt thereof:

(Ie)

wherein $R^1$, $R^2$, $R^3$, $R^5$ and $R^6$ are as defined in Formula I, and X is selected from $CH_2$ and O.

6. The compound according to claim 5 wherein $R^1$, $R^2$ $R^3$ are each independently selected from the group consisting of:
(1) hydrogen,
(2) $C_1$-$C_6$ alkoxy,
(3) heteroaryl,
(4) halogen,
(5) aryl
(6) CN,
(7) $C_1$-$C_6$ alkyl,
(8) $C_2$-$C_6$ alkene,
(9)

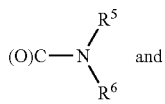
and

(10) $C(O)_2$—$R^4$,
said heteroaryl and aryl is optionally substituted with one or more substituents selected from selected from $R^5$ and $R^6$.

7. The compound according to claim 6 wherein $R^1$, $R^2$ and $R^3$ are each independently selected from the group consisting of:
(1) hydrogen,
(2) $C_1$-$C_6$ alkoxy,
(3) heteroaryl,
(4) halogen,
(5) $C_2$-$C_6$ alkene,
(6)

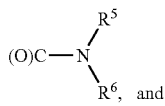
and (7) $C(O)_2$—$R^4$,
said heteroaryl is optionally substituted with one or more substituents selected from selected from $R^5$ and $R^6$.

8. The compound according to claim 7 wherein $R^4$ is selected from the group consisting of:
(1) aryl,
(2) $C_1$-$C_6$ alkyl-aryl,
(3) $C_3$-$C_6$ cycloalkyl,
(4) $C_1$-$C_6$ alkyl, (5) C$_1$-C$_6$ alkyl-C$_3$-C$_6$ cycloalkyl, (6)

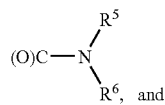

(7) C(O)—R$^5$, said aryl and cycloalkyl are each optionally substituted with one or more substituents selected from R$^5$ and R$^6$.

9. The compound according to claim 6 wherein
R$^5$ and R$^6$ are each independently selected from the group consisting of:
(1) hydrogen,
(2) halogen,
(3) C$_1$-C$_6$ alkoxy,
(4) C$_3$-C$_6$ cycloalkyl,
(5)

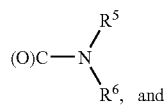

(6) C$_1$-C$_6$ alkyl;

said heteroaryl and aryl are each optionally substituted with one or more substituents selected from R$^7$, or R$^5$ and R$^6$, together with the nitrogen atom to which they are attached, can join to form a 5- to 7-membered heteroaryl or heterocycloalkyl.

10. The compound according to claim 1, represented by

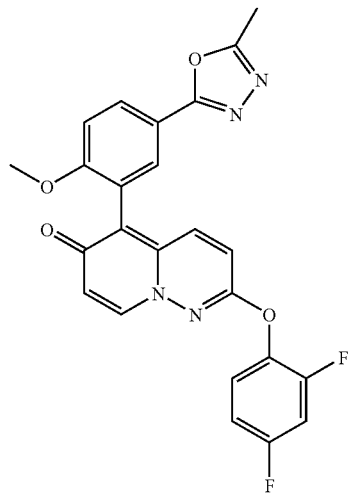

-continued

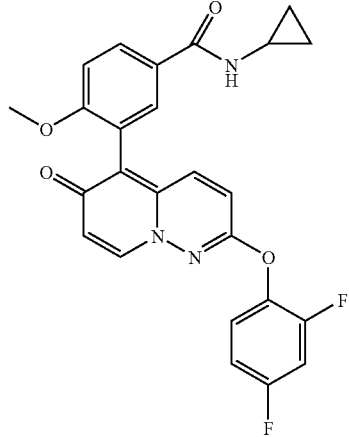

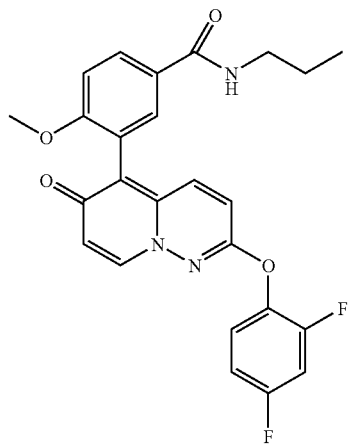

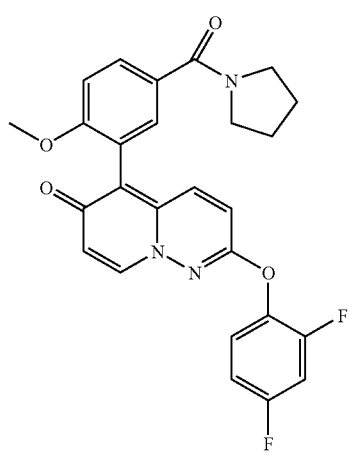

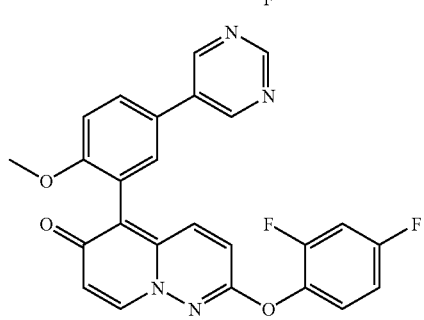

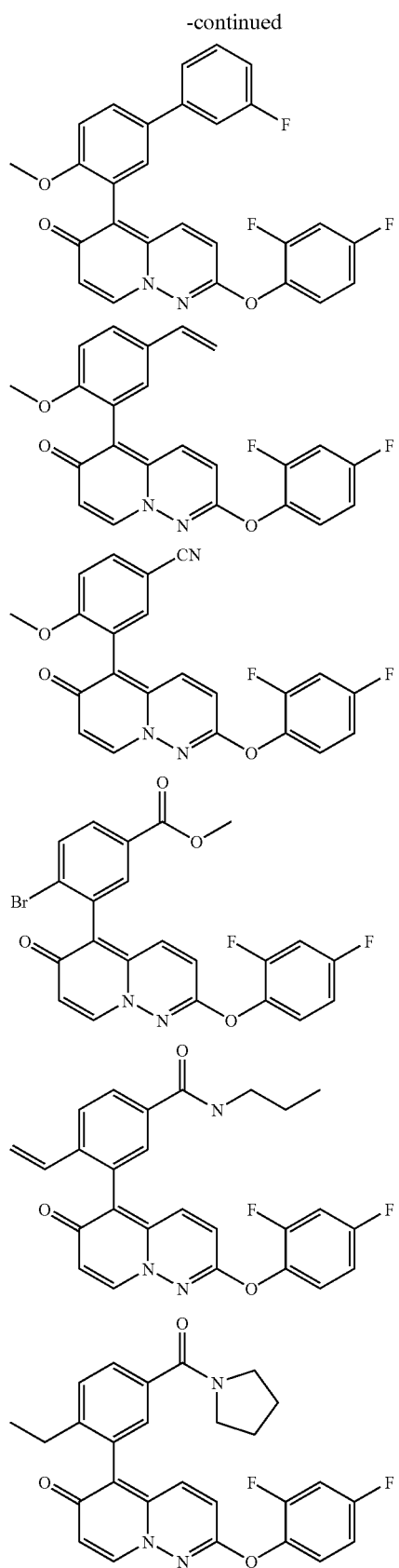
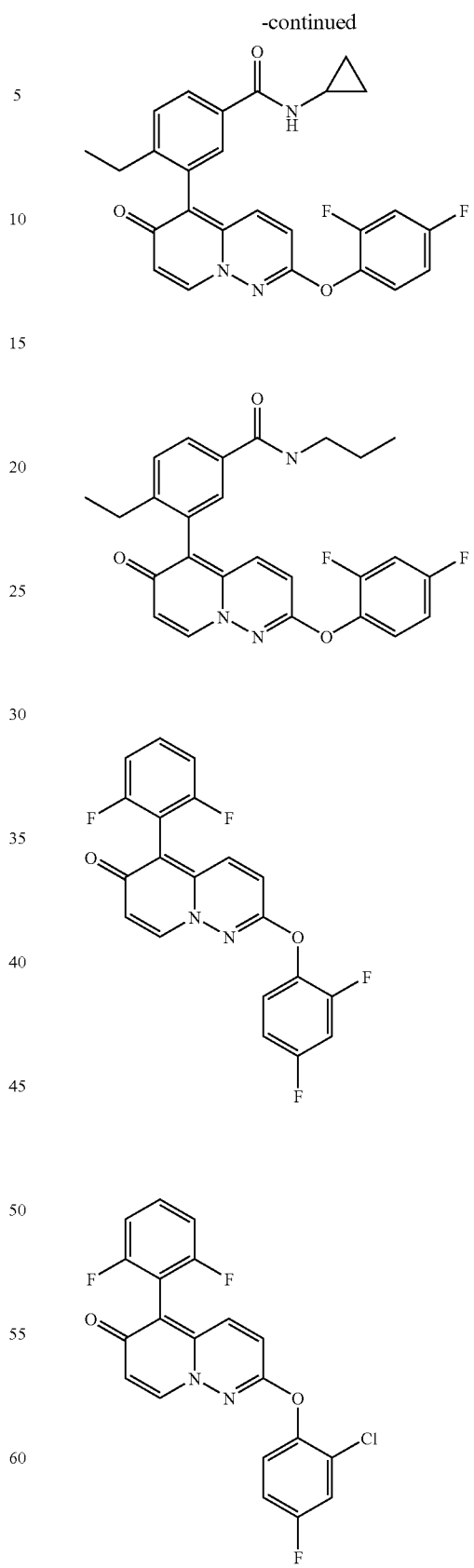

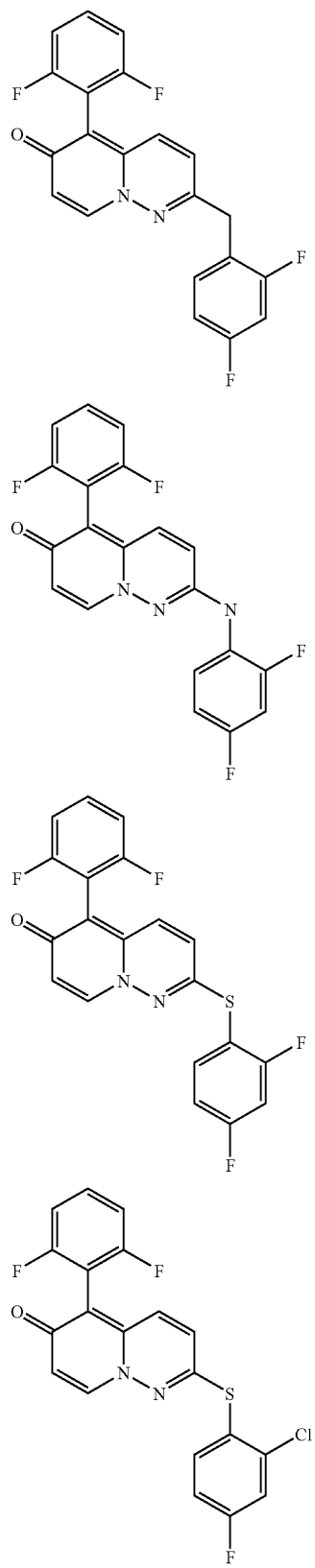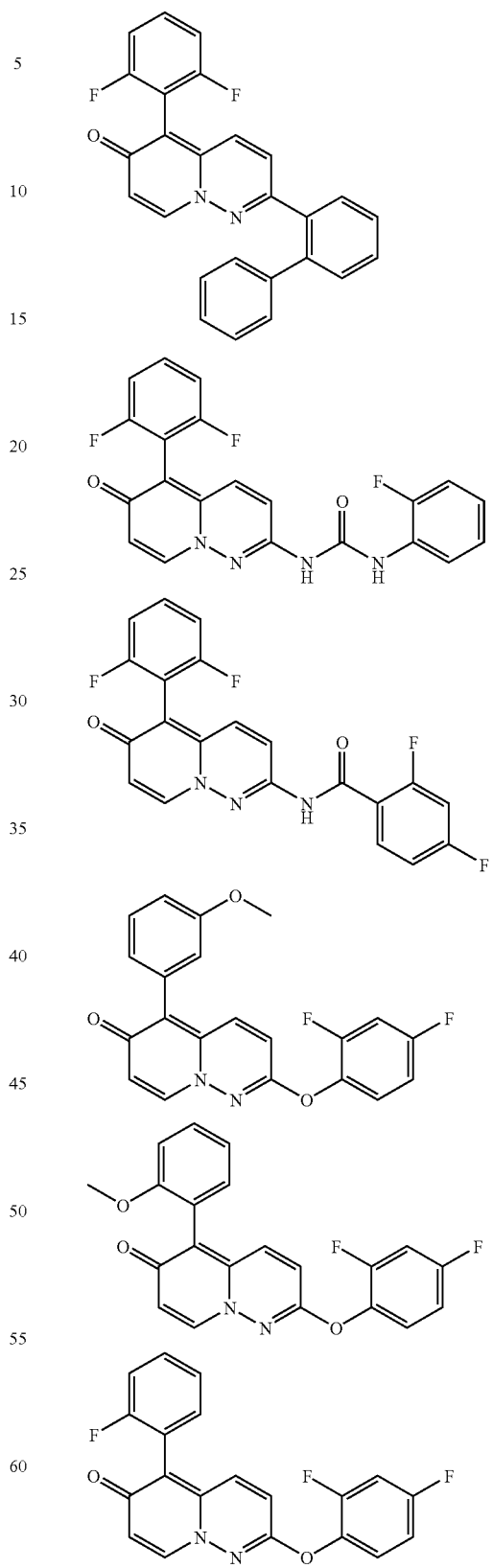

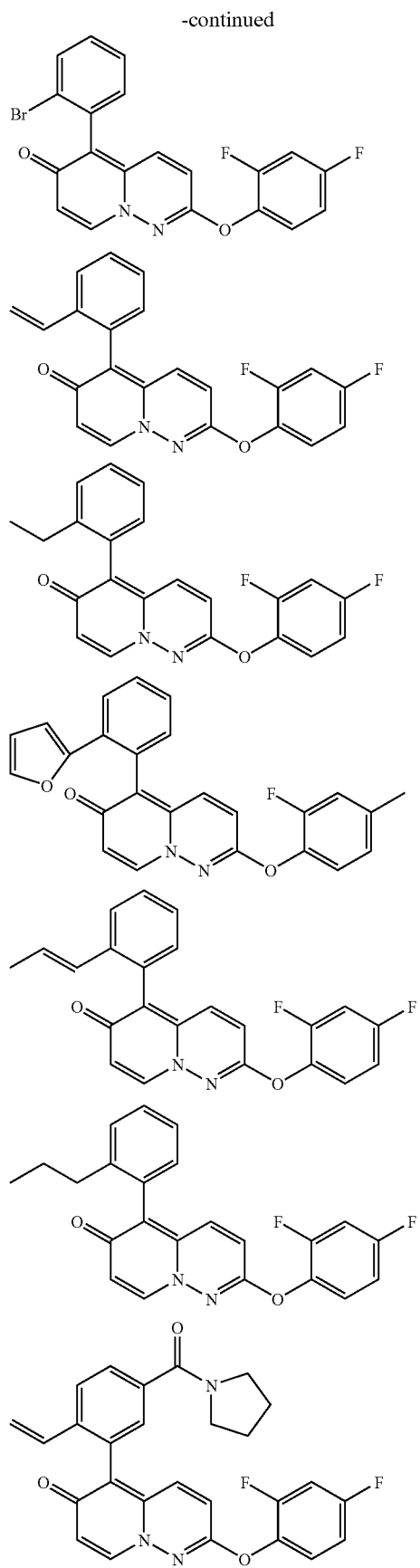
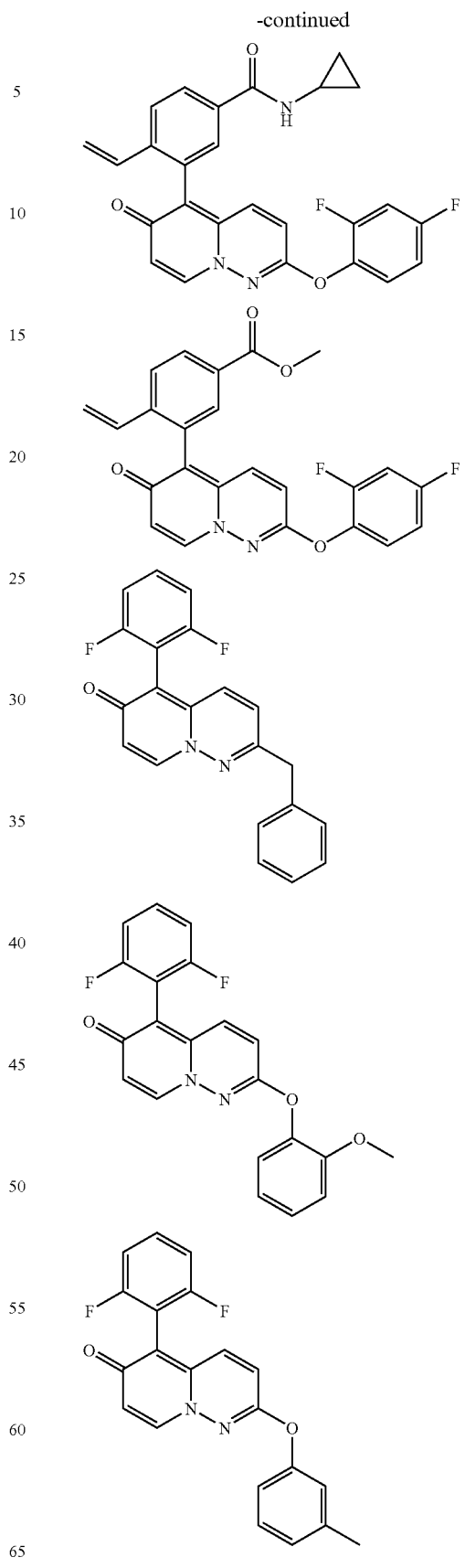

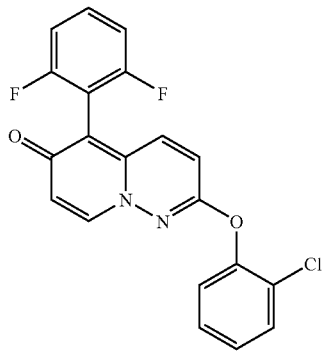
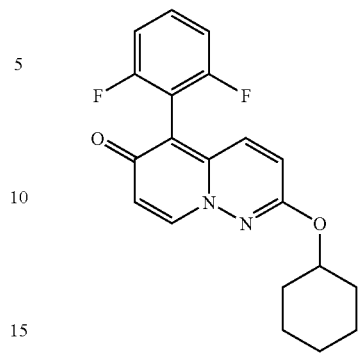
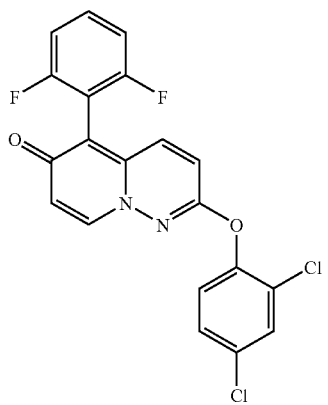
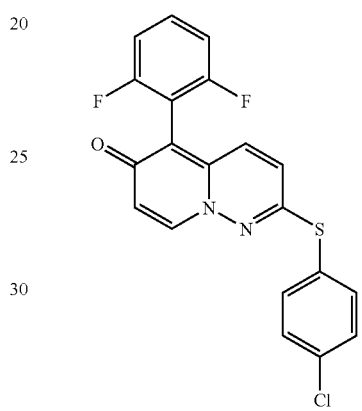
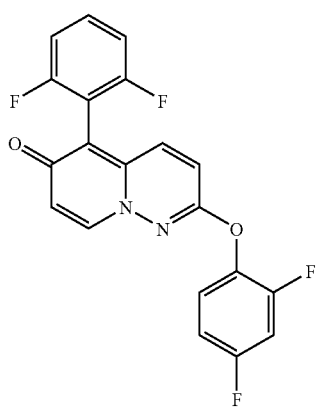
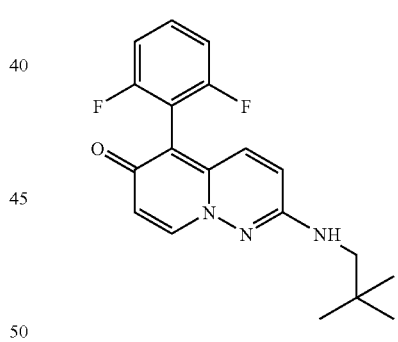
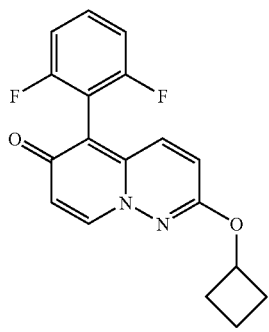
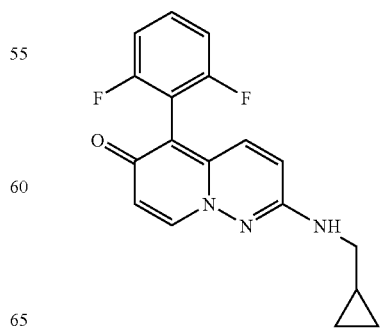

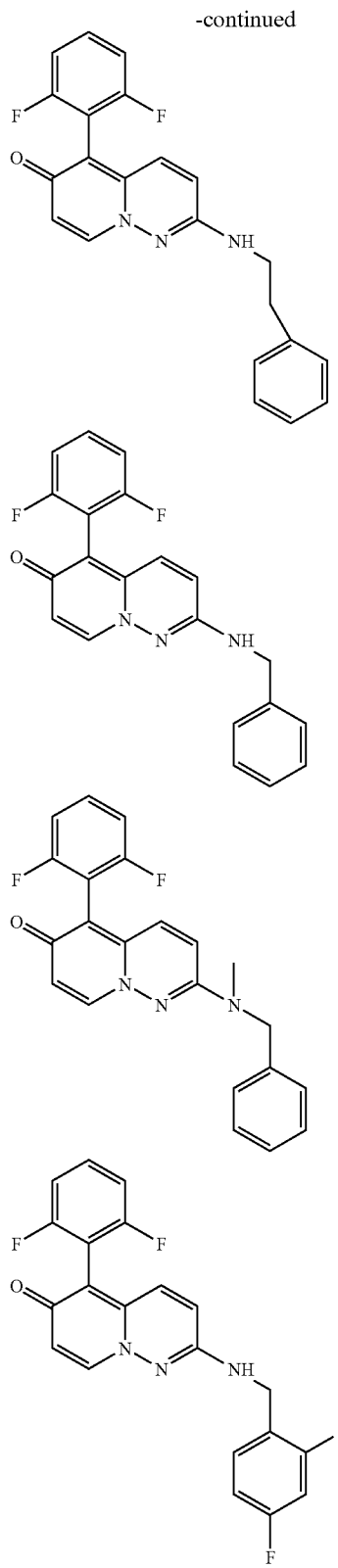
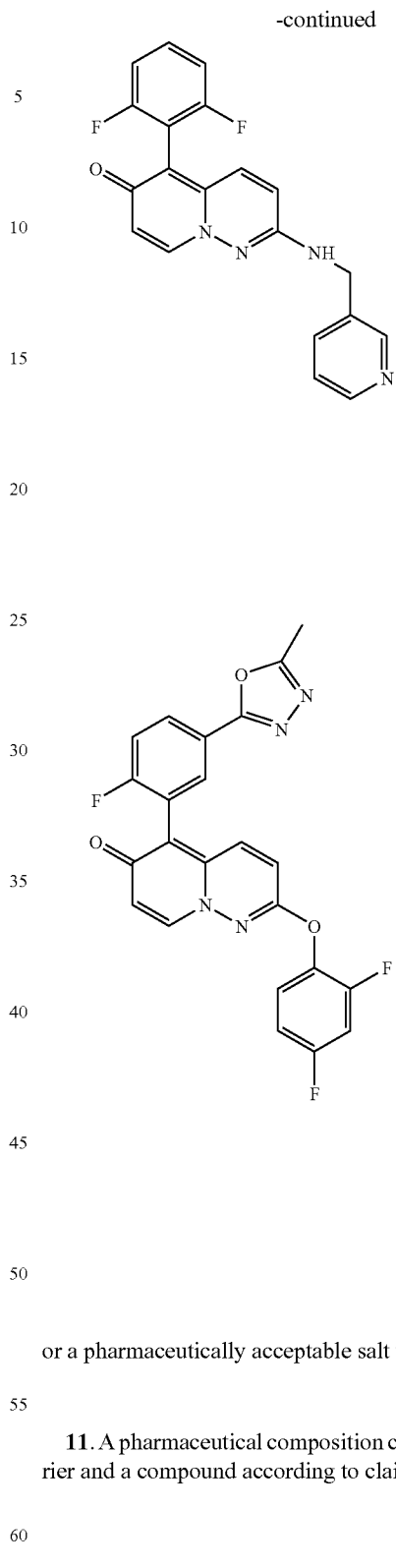
or a pharmaceutically acceptable salt thereof.
11. A pharmaceutical composition comprising an inert carrier and a compound according to claim 1.
* * * * *